United States Patent
Schrezenmeir et al.

(10) Patent No.: US 10,786,452 B2
(45) Date of Patent: Sep. 29, 2020

(54) SUGAR-DEPLETED FRUIT OR VEGETABLE JUICE AND JUICE-RETAINING FRUIT OR VEGETABLE DERIVED MATTER, METHODS OF PRODUCING THE SAME AND THE USE THEREOF TO MAINTAIN HEALTH AND TO TREAT AND PREVENT MEDICAL AILMENTS

(71) Applicant: NOFIMA AS, As (NO)

(72) Inventors: Jurgen Schrezenmeir, Karlsruhe (DE); Svein Halvor Knutsen, Ski (NO); Simon Ballance, Royken (NO)

(73) Assignee: NOFIMA AS, As (NO)

( * ) Notice: Subject to any disclaimer, the term of this patent is extended or adjusted under 35 U.S.C. 154(b) by 0 days.

(21) Appl. No.: 16/574,766

(22) Filed: Sep. 18, 2019

(65) Prior Publication Data

US 2020/0009048 A1 Jan. 9, 2020

Related U.S. Application Data

(62) Division of application No. 15/515,883, filed as application No. PCT/GB2015/052880 on Oct. 1, 2015, now Pat. No. 10,471,009.

(30) Foreign Application Priority Data

Oct. 1, 2014 (GB) .................................. 1417386.8

(51) Int. Cl.
| | | |
|---|---|---|
| A61K 33/00 | (2006.01) |
| A23L 2/84 | (2006.01) |
| A61K 9/00 | (2006.01) |
| A23L 2/52 | (2006.01) |
| A61K 31/191 | (2006.01) |
| A23L 33/00 | (2016.01) |
| A61K 33/06 | (2006.01) |

(52) U.S. Cl.
CPC .............. *A61K 9/0095* (2013.01); *A23L 2/52* (2013.01); *A23L 2/84* (2013.01); *A23L 33/30* (2016.08); *A61K 31/191* (2013.01); *A61K 33/00* (2013.01); *A61K 33/06* (2013.01); *A23V 2002/00* (2013.01)

(58) Field of Classification Search
CPC ... A23L 2/52; A23L 2/84; A23L 33/30; A23V 2002/00; A61K 33/00; A61K 33/06; A61K 9/0095
See application file for complete search history.

(56) References Cited

U.S. PATENT DOCUMENTS

| | | |
|---|---|---|
| 3,935,071 A | 1/1976 | Bergmeyer et al. |
| 4,356,195 A | 10/1982 | Kahn et al. |
| 4,675,191 A | 6/1987 | Villettaz |
| 4,722,847 A | 2/1988 | Heckert |
| 5,800,830 A | 9/1998 | Asano et al. |
| 2002/0122866 A1 | 9/2002 | Palaniappan et al. |
| 2005/0058763 A1 | 3/2005 | Cetrulo et al. |
| 2005/0123650 A1 | 6/2005 | Parente et al. |
| 2008/0044531 A1 | 2/2008 | Blase et al. |
| 2008/0248100 A1 | 10/2008 | Liu et al. |
| 2009/0214620 A1 | 8/2009 | Wyrobnik et al. |
| 2009/0311232 A1 | 12/2009 | Wyrobnik et al. |
| 2012/0114791 A1 | 5/2012 | Van Den Brink et al. |
| 2013/0287871 A1 | 10/2013 | Coy |
| 2017/0296468 A1 | 10/2017 | Schrezenmeir et al. |

FOREIGN PATENT DOCUMENTS

| | | |
|---|---|---|
| CH | 632137 A5 | 9/1982 |
| CN | 102450722 A | 5/2012 |
| DE | 1406087 C1 | 7/1995 |
| DE | 102008018608 | 10/2009 |
| EP | 0032010 A2 | 7/1981 |
| EP | 0554488 A1 | 8/1993 |
| EP | 0934702 A1 | 8/1999 |
| EP | 2127667 A1 | 12/2009 |
| EP | 2415863 A1 | 2/2012 |
| EP | 2508083 A1 | 10/2012 |
| GB | 626848 | 7/1949 |
| GB | 1356283 | 3/1970 |
| GB | 2207335 A | 2/1989 |

(Continued)

OTHER PUBLICATIONS

902 KAR 45:040 (Kentucky Legislature); "Carbonated Beverages"; Relates to KRS Chapter 217, Statutory Authority: KRS Chapter 13B, 194.50, 217.125, EO 96-862; 5 pages; (1996); www.lrc.ky.gov/kar/TITLE902.HTM.

Abernathy, et al.; "Apocalypse Beer: How to Ferment Anything"; The Brew Site; [online] retrieved on Nov. 16, 2018 from HTTP://www.thebrwsite.com/apocalypse-beer-ferment-anything/; 9 pages; (Year 2012).

(Continued)

*Primary Examiner* — Ernst V Arnold

(74) *Attorney, Agent, or Firm* — Cantor Colburn LLP

(57) ABSTRACT

Described herein is a sugar-depleted fruit or vegetable juice product, wherein said juice product is a fruit or vegetable juice or juice-retaining fruit or vegetable derived matter, wherein said juice product contains at least about 5 g/l gluconic acid and said juice product contains any two or three, of (i) at least about 0.5 g/l $Ca^{2+}$, (ii) at least about 1 g/l $K^+$, and (iii) at least about 0.1 g/l $Mg^{2+}$. Also provided are methods of producing the same and the use thereof to assist in maintaining the health and well-being of a subject and in the treatment and prevention of medical ailments, specifically those associated with the over-consumption of glucose and/or sucrose or inappropriate metabolism of glucose, e.g. metabolic syndrome, diabetes mellitus type II, obesity, dyslipidemia, insulin resistance, hypertension and liver steatosis.

28 Claims, 2 Drawing Sheets

(56) References Cited

FOREIGN PATENT DOCUMENTS

Figure 1:
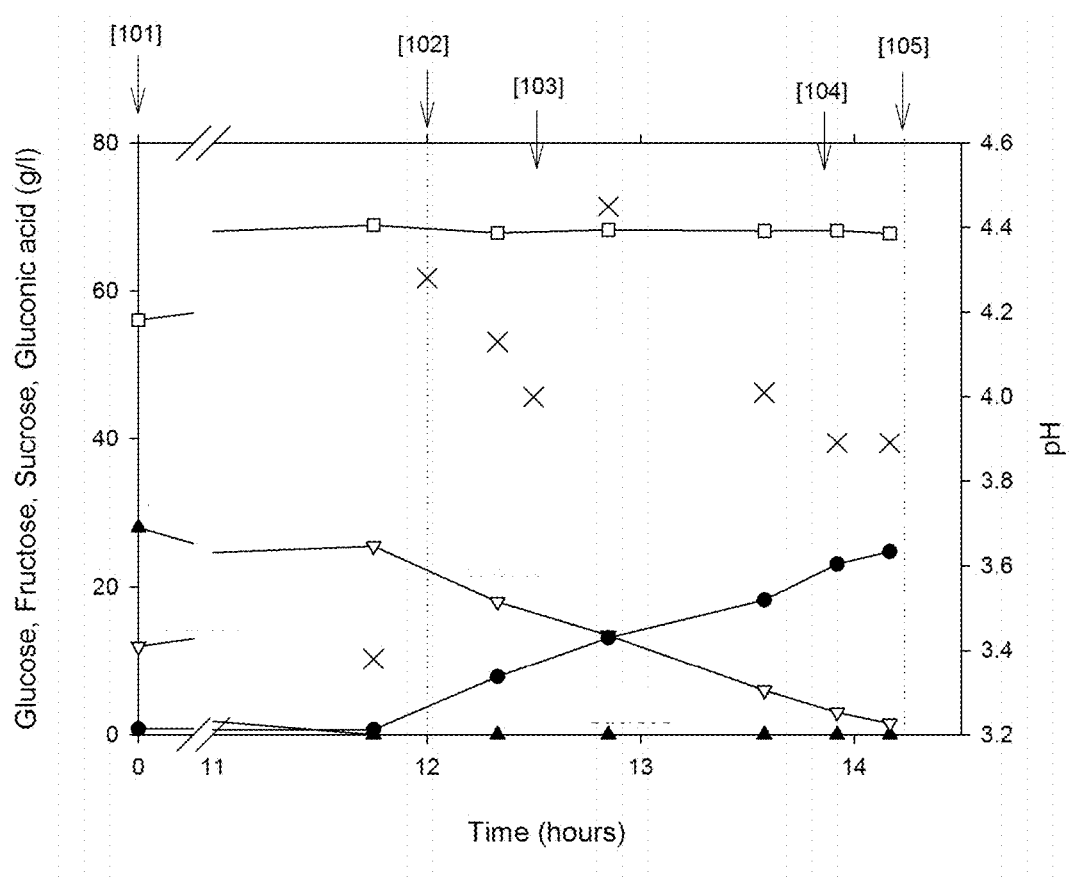

| | | | |
|---|---|---|---|
| GB | 2465814 A | 6/2010 | |
| JP | 57122775 | 7/1982 | |
| RU | 2009111952 A | 10/2010 | |
| WO | 199203066 A1 | 3/1992 | |
| WO | 199406412 A1 | 3/1994 | |
| WO | 2007061918 A2 | 5/2007 | |
| WO | 2008102336 | 8/2008 | |
| WO | 2011003888 A1 | 1/2011 | |
| WO | 2012167872 A1 | 12/2012 | |
| WO | 2014000746 A1 | 1/2014 | |
| WO | 2015000580 A2 | 1/2015 | |
| ZA | 8504565 A1 | 2/1986 | |

OTHER PUBLICATIONS

Ameyama, et al.; "5-Keto-D-fructose Reductase of Gluconobacter Industrius: Purification, Crystallization and Properties"; Agric. Biol. Chem., 45(4), pp. 863-869; (1981).

Aziz, et al.; "Production and Application of Glucose-fructose Oxidoreductase for Conversion of Pineapple Juice Sugars"; African Journal of Microbiology Research; 5(28); pp. 5046-5052; (2011).

Bankar et al.; "Glucose Oxidase—An Overview"; Biotehnology Advances; 27(4); pp. 489-501; Abstract only; Jul.-Aug. (2009).

International Search Report and Written Opinion; International Application No. PCT/GB2015/052880; International Filing Date Oct. 1, 2015; dated Jan. 12, 2016; 13 pages.

Pickering, Gary J.; "Optimising Glucose Conversion in the Production of Reduced Alcohol Wine Using Glucose Oxidase"; Food Research International; 31(10) pp. 685-692; (1998).

Ramachandran et al.; "Gluconic Acid: Properties, Applications and Microbial Production"; Biotechnol.; 44(2); pp. 185-195; (2006).

Sims, Josh; "Bionade: The Health Drink That Looks Like Beer"; The Independent; 3 pages, Nov. 27, 2007.

Singer, Raphael; "New Ways for Beverage Formulators to Reduce Bitterness and Balance Sourness"; Technical White Paper presented by Jungbunzlauer; 12 pages; Published Feb. 7, 2011; www.jungbunzlauer.com.

Singh et al. "Evaluating the Buffering Capacity of Various Soft Drinks, Fruit Juices and Tea"; J. Consery Dent; 13(3); pp. 129-131; (2010).

Singh et al.; "Biotechnological Production of Gluconic Acid: Future Implications"; Appl Microbiol Biotechnol; 75; pp. 713-722; (2007).

Stetten et al.; "The Metabolism of Gluconic Acid"; J. Biol. Chem.; 187; pp. 241-252; (1950).

Tsukahara et al.; "Stimulation of Butyrate Production by Gluconic Acid in Batch Culture of Pig Cecal Digesta and Identification of Butyrate-Producing Bacteria"; The Journal of Nutrition; 132, pp. 2229-2234; (2002).

Wardman, Rhyan C.; Thesis; "Determination and Removal of Gluconic Acid in Reduced Alcohol Wine and High Acid Grape Juice"; submitted at Lincoln University; 121 pages; (1995).

Wong et al.; "Glucose Oxidase: Natural Occurrence, Function, Properties and Industrial Applications"; Appl Microbiol Biotechnol; 78; pp. 927-938; (2008).

Zachariou et al.; "Glucose-Fructose Oxidoreductase, a New Enzyme Isolated From Zymomonas Mobilis That Is Responsible for Sorbitol Production"; Journal of Bacteriology; 167; pp. 863-869; (1986).

SUGAR-DEPLETED FRUIT OR VEGETABLE JUICE AND JUICE-RETAINING FRUIT OR VEGETABLE DERIVED MATTER, METHODS OF PRODUCING THE SAME AND THE USE THEREOF TO MAINTAIN HEALTH AND TO TREAT AND PREVENT MEDICAL AILMENTS

CROSS-REFERENCE TO RELATED APPLICATIONS

This application is a Divisional of U.S. application Ser. No. 15/515,883 filed on Mar. 30, 2017, now U.S. Pat. No. 10,471,009 which is a National Stage application of PCT/GB2015/052880, filed Oct. 1, 2015, which claims the benefit of GB Application No. 1417386.8, filed Oct. 1, 2014, both of which are incorporated by reference herein in their entirety.

DETAILED DESCRIPTION

The present invention provides improved sugar-depleted fruit or vegetable juice and sugar-depleted juice-retaining fruit or vegetable derived matter, methods of producing the same and the use thereof to assist in maintaining the health and well-being of a subject and in the treatment and prevention of medical ailments, specifically those associated with the over-consumption of glucose and/or sucrose or inappropriate metabolism of glucose, e.g. metabolic syndrome, diabetes mellitus type II, obesity, dyslipidemia, insulin resistance, hypertension and liver steatosis.

For convenience the term "juice product" is used herein to encompass both the fruit or vegetable juice and juice-retaining fruit or vegetable derived matter to which the invention relates in general. The term "sugar-depleted juice product" is used herein analogously.

The "sugar-depleted juice product" of the invention may be prepared by treating fruit or vegetable juice or juice-retaining fruit or vegetable derived matter (a "juice product") with a plurality of enzymes and supplementing the juice with defined amounts of particular metal ions, thereby resulting in a modified juice product containing reduced amounts of free glucose and optionally sucrose, e.g. substantially or essentially no free glucose or optionally sucrose, but an amount of gluconic acid corresponding to the amount by which free glucose and optionally sucrose in the juice product is reduced, e.g. the amount of free glucose and optionally sucrose in the juice product prior to the enzyme treatment, and amounts of said metal ions that ensure palatability and contribute to the nutritional and therapeutic value of the modified juice product. The presence of gluconic acid in combination with reduced amounts, preferably the substantial or essential absence, of sucrose and free glucose means the modified juice product of the invention has a surprisingly advantageous glycaemic profile and thus renders the modified juice product useful as part of a healthy diet in healthy subjects, and also surprisingly effective in treating subjects with or at risk of developing complex metabolic disorders associated with the over-consumption of glucose and/or sucrose and/or inappropriate metabolism of glucose including metabolic syndrome, diabetes, obesity, dyslipidemia, insulin resistance, hypertension and liver steatosis, on account of its favourable insulin response and/or favourable effect on insulin sensitivity.

It is now well appreciated that a diet rich in simple sugars such as glucose and sucrose can lead to health problems, in particular metabolic conditions including diabetes mellitus type II, metabolic syndrome and obesity. It is also well established that the consumption of fruit and vegetables, including the juices thereof, has certain health benefits, potentially including the prevention of certain cancers and heart disease. However, fruit and vegetable juice products are also rich sources of simple sugars, thus diminishing the overall benefit to health of such foodstuffs. Consequently, it would potentially be advantageous to lower the sugar content of fruit and vegetable juice products if this can be done without detrimentally affecting palatability and leaving the other components of the juice product substantially unaffected.

To this end there has been proposed various techniques to reduce the levels of free glucose in fruit juices.

CH 632137 describes the microbial fermentation of juices to convert sugars to alcohols and the distillation of the alcohols so produced. Procedures such as these radically alter the flavour and nature of the juice. To address this problem EP 032010 and EP 0554488 describe complex procedures in which microbes degrade juice sugars without fermentation into alcohols.

U.S. Pat. No. 3,935,071 describes the conversion of glucose in fruit juices and other foodstuffs to gluconic acid through the action of glucose oxidase. The value of such glucose-depleted foodstuffs for diabetes is mentioned.

An article in A-Magasinet (Norway), Issue 21 Sep. 2007, describes a speculative approach in which fruit juice is treated with three enzymes to split sucrose into fructose and glucose, to convert fructose to glucose and then to convert glucose to gluconic acid.

Aziz, M. G., et al., 2011, African Journal of Microbiology Research, Vol 5(28), 5046-5052, describes the use of glucose-fructose oxidoreductase and invertase to convert pineapple juice sugars to gluconic acid and sorbitol. Sugar conversion was incomplete and the palatability of the resulting product was not assessed.

It has now been found that simply reducing or removing free glucose from fruit and vegetable juices results in a less than palatable product that requires the introduction of artificial sweeteners and flavourings or a product which fails to retain the flavour and mouth-feel of the unmodified juice. These problems are exacerbated when sucrose and/or free fructose is also reduced/removed from the juice.

It has now been found however that fruit or vegetable juice products in accordance with the invention can be sugar-depleted, e.g. rendered substantially or essentially devoid of glucose and sucrose, by treatment with (i) an enzyme which hydrolyses sucrose into glucose and fructose (e.g. invertase) and (ii) an enzyme that converts glucose into gluconic acid (e.g. glucose oxidase) and, upon supplementation with particular combinations of metal ions, a sugar-depleted juice product with superior palatability is obtained which retains sufficiently the taste, flavour and mouth-feel of the unmodified juice product.

As used herein the term "free glucose" refers to glucose that is not covalently bound to another saccharide molecule, in other words glucose which is not part of a di-, oligo- or poly-saccharide, e.g. including but not limited to sucrose, amylose, amylopectin, pectin and cellulose.

As used herein, the term "gluconic acid" is generic and represents all the equilibrium species of gluconic acid in an aqueous medium—e.g. lactone forms (e.g. D-gluconic acid δ-lactone and D-gluconic acid γ-lactone), gluconate salt forms and the acid form. Without wishing to be bound by theory, it is believed that the supplementation of the sugar-depleted juice product of the invention with the above described metal ions causes a favourable shift in the amounts of gluconate-metal salts present in the sugar-depleted juice product and it is these salt profiles that promote the retention of the flavour and mouth-feel of the unmodified juice product.

In addition it has been found that the comparatively high gluconic acid content of a modified juice in which substantially, e.g. essentially, all of the free glucose and the glucose in sucrose has been converted to gluconic acid offers a product with a glycaemic response, a glycaemic index, a glycaemic load and an insulin response which are significantly lower than those of an untreated juice, i.e. a more favourable glycaemic profile and lower available carbohydrate content, respectively, which in turn reduces the amount of dietary energy provided by the product.

By way of example, for grape juice, the relative area under the glycaemic curve in response to the consumption of grape juice treated in accordance with the invention is less than 16% of that of the glycaemic curve in response to untreated juice. In the case of apple juice, the relative area under the glycaemic curve in response to consumption of apple juice treated in accordance with the invention is 30% of that of the glycaemic curve in response to untreated juice. Other juices would display corresponding differences in relative area under the glycaemic curve between modified and unmodified forms, although the exact reductions will depend on the precise content of glucose and other sugars contributing to glycaemic response.

The difference between the insulin response to such a juice product of the invention as compared to the insulin response to an unmodified juice product is may be more pronounced than that of the glucose response. A juice product of the invention may also increase insulin sensitivity.

Such a modified juice product is therefore surprisingly suited to the treatment and prevention of complex metabolic disorders associated with the over-consumption of glucose and/or sucrose or the inappropriate metabolism of glucose including metabolic syndrome, diabetes, obesity, dyslipidemia, insulin resistance, hypertension and liver steatosis.

Thus, it can be seen that the present invention provides a palatable modified juice product of superior nutritional value and therapeutic properties.

Therefore, in a first aspect of the present invention there is provided a sugar-depleted fruit or vegetable juice product, wherein said juice product is a fruit or vegetable juice or juice-retaining fruit or vegetable derived matter, wherein said juice product contains at least about 5 g/l gluconic acid and said juice product contains any two or three, of
  (i) at least about 0.5 g/l $Ca^{2+}$,
  (ii) at least about 1 g/l $K^+$, and
  (iii) at least about 0.1 g/l $Mg^{2+}$.

By "juice" it is meant a liquid that has a make-up essentially in direct correlation to the liquid part of a ripe (or at least human edible) fruit or a vegetable that has been extracted in a method comprising at least one mechanical means of juice extraction, e.g. by pressing, pulping, mashing, macerating, liquefying and/or sieving. Preferably a juice in accordance with the invention is the liquid part of a ripe fruit or a vegetable that has been extracted in a method comprising at least one mechanical means of juice extraction, but in other embodiments it is a concentrated or diluted form thereof. The reference to diluted forms includes extended juice products, e.g. those referred to as "nectars", which typically comprise about 50% to about 90%, e.g. about 50% to about 80% or about 50% to about 70%, juice. In accordance with the invention the fruit or vegetable derived constituents of these diluted or concentrated forms are in direct correlation to the liquid part of a ripe fruit or a vegetable that has been extracted in a method comprising at least one mechanical means of juice extraction because essentially the only component added or removed from the extracted liquid is water. The extraction methods described above may also comprise enzyme treatments which breakdown biopolymers. Conveniently the term "juice" can be taken as that defined by the standards of labelling in the EU (no sugar added etc.).

By "juice-retaining fruit or vegetable derived matter" it is meant a substance substantially, preferably essentially, made up of, e.g. consisting of, fruit or vegetable derived matter wherein substantially, preferably essentially, none of the juice of the fruit or vegetable has been removed. A juice-retaining fruit or vegetable derived matter of the invention includes purees, pastes, and stews.

By "sugar-depleted" it is meant that a juice product has a reduced amount of free glucose and optionally a reduced amount of sucrose that together result in a reduced glycaemic response in a subject as measured by the area under the curve (AUC) of a subject's blood glucose (preferably capillary blood glucose) levels over time, preferably over about 15 mins, 30 mins, 45 mins, 60 mins, 75 mins, 90 mins, 105 mins, 120 mins, 150 mins, 180 mins, 210 mins or 240 mins immediately following consumption of the sugar-depleted juice product, relative to a juice product that has been prepared from the same fruit or vegetable in the same way but which is not sugar-depleted. Preferably the AUC is calculated as the incremental AUC (iAUC), i.e. all area below the curve but above the fasting blood glucose concentration. Preferably the AUC, e.g. the iAUC, is calculated over about 120 mins. The glycaemic response for each product should be determine in the same way.

The sugar-depleted juice product preferably results in an area under the curve as defined above in response to its consumption that is no more than 75%, e.g. no more than about 70, 65, 60, 55, 50, 48, 46, 44, 42, 40, 38, 36, 34, 32, 30, 28, 26, 24, 22, 20, 18, 16, 14, 12, 10, 5 or 1% of that of a juice product that has been prepared from the same fruit or vegetable in the same way but which is not sugar-depleted.

Expressed alternatively, "sugar depleted" means that a juice product has a reduced amount of free glucose and optionally a reduced amount of sucrose that together result in the juice product having a reduced glycaemic load relative to that of a juice product that has been prepared from the same fruit or vegetable in the same way but which is not sugar-depleted. The sugar-depleted juice product preferably has a glycaemic load which is no more than 75%, e.g. no more than about 70, 65, 60, 55, 50, 48, 46, 44, 42, 40, 38, 36, 34, 32, 30, 28, 26, 24, 22, 20, 18, 16, 14, 12, 10, 5 or 1%, of that of a juice product that has been prepared from the same fruit or vegetable in the same way but which is not sugar-depleted. The glycaemic load of each product should be determined in the same way.

For the purposes of the invention, the glycaemic load of a foodstuff is calculated as the amount of available carbohydrate in a standard portion of the foodstuff multiplied by the glycaemic index (GI) of the foodstuff divided by 100. For the juice product of the invention a standard portion size may be taken as about 250 ml or about 250 g as appropriate.

For the purposes of the invention the GI of a foodstuff is defined as the iAUC of a blood glucose response curve over about 120 mins after consumption of a 50 g available-carbohydrate portion of a foodstuff expressed as a percentage of that after 50 g oral glucose. For the purposes of the invention available carbohydrate is that fraction of carbohydrate that is absorbed across the gastrointestinal tract and enters into intermediary metabolism. It does not include dietary fibre.

Expressed alternatively still, "sugar depleted" means that a juice product has a reduced amount of free glucose and optionally a reduced amount of sucrose that together result in the juice product having a reduced glycaemic index relative to that of a juice product that has been prepared from the same fruit or vegetable in the same way but which is not sugar-depleted. The sugar-depleted juice preferably has a glycaemic index which is no more than 75%, e.g. no more than about 70, 65, 60, 55, 50, 48, 46, 44, 42, 40, 38, 36, 34, 32, 30, 28, 26, 24, 22, 20, 18, 16, 14, 12, 10, 5 or 1%, of that of a juice product that has been prepared from the same fruit or vegetable in the same way but which is not sugar-depleted.

This may also be expressed as a juice product that has a lower mass concentration ratio of free glucose to non-saccharide soluble components and optionally a lower mass concentration ratio of sucrose to non-saccharide soluble components than the corresponding ratios of a juice product that has been prepared from the same fruit or vegetable in the same way but which is not sugar-depleted. In these embodiments "lower" means a mass concentration ratio of free glucose/sucrose (individually and as appropriate) to non-saccharide soluble components which is no more than 75%, e.g. no more than about 70, 65, 60, 55, 50, 48, 46, 44, 42, 40, 38, 36, 34, 32, 30, 28, 26, 24, 22, 20, 18, 16, 14, 12, 10, 5 or 1% of that of a juice product that has been prepared from the same fruit or vegetable in the same way but which is not sugar-depleted.

Mass concentration is an indication of the mass of a first substance present in a defined mass or volume of a second substance. Mass concentration may therefore be expressed as grams per litre ("g/l"), grams per kilogram ("g/kg"), parts-per-million (ppm, i.e. mg of solute per litre of solvent); "% w/v"; "% w/w, "g/100ml"; or the like.

More specifically, "sugar-depleted" means that the mass concentrations of free glucose and optionally sucrose are no more than about 75% of the mass concentrations of free glucose and optionally sucrose typically present in the same juice product that has been prepared from the same fruit or vegetable in the same way but which is not sugar-depleted, e.g. no more than about 50, 40, 30, 25, 20, 15, 10, 9, 8, 7, 6, 5, 4, 3, 2, or 1% of the mass concentrations of free glucose and optionally sucrose typically present in the same juice product that has been prepared from the same fruit or vegetable in the same way but which is not sugar-depleted. The extent by which the mass concentrations of free glucose and optionally sucrose may be lower in the sugar-depleted juice product as compared to a juice product which is not sugar-depleted need not be the same. Therefore, the mass concentration of free glucose in the sugar-depleted juice product may be no more than about any one of 75, 50, 40, 30, 25, 20, 15, 10, 9, 8, 7, 6, 5, 4, 3, 2, or 1% the mass concentrations of free glucose typically present in the same juice product that has been prepared from the same fruit or vegetable in the same way but which is not sugar-depleted, and/or the mass concentration of sucrose in the sugar-depleted juice product may be no more than about any one of 75, 50, 40, 30, 25, 20, 15, 10, 9, 8, 7, 6, 5, 4, 3, 2, or 1% the mass concentration of sucrose typically present in the same juice product that has been prepared from the same fruit or vegetable in the same way but which is not sugar-depleted.

More simply "sugar depleted" means the mass concentrations of free glucose and optionally sucrose in the sugar-depleted juice product is (are independently) reduced by at least about 25, 50, 60, 70, 75, 80, 85, 90, 91, 92, 93, 94, 95, 96, 97, 98 or 99% as compared to the mass concentrations of free glucose and optionally sucrose in the same juice product that has been prepared from the same fruit or vegetable in the same way but which is not sugar-depleted.

In the case of a sugar-depleted juice, the above features should be interpreted by reference to the liquid part of the same fruit or vegetable that has been extracted in a method comprising at least one mechanical means of juice extraction, as defined above.

In certain embodiments the combined mass concentrations of the free glucose and sucrose in the sugar-depleted juice product of the invention is no more than about 20 g/l, e.g. no more than about 19, 18, 17, 16, 15, 14, 13, 12, 11, 10, 9, 8, 7, 6, 5, 4, 3, 2, 1, 0.5, 0.1, 0.05, 0.01 g/l, when said juice product is adjusted in volume with water to give a gluconic acid concentration of about 5 g/l or the specific concentrations disclosed below (e.g. about 6, 8, 10, 12, 14, 16, 18, 20, 22, 24, 26, 28, 30, 32, 34, 36, 38, 40, 45, 50, 55, 60, 65, 70, 75, 80, 85, 90, 95 or 100 g/l).

The ratio of free glucose to sucrose within these combined mass concentrations is not restricted and so may be 1:99 to 99:1, e.g. 1:95 to 95:1, 1:90 to 90:1, 1:85 to 85:1, 1:80 to 80:1, 1:75 to 75:1, 1:70 to 70:1, 1:65 to 65:1, 1:60 to 60:1, 1:55 to 55:1, 1:50 to 50:1, 1:45 to 45:1, 1:40 to 40:1, 1:35 to 35:1, 1:30 to 30:1, 1:25 to 25:1, 1:20 to 20:1, 1:15 to 15:1, 1:10 to 10:1, 1:9 to 9:1, 1:8 to 8:1, 1:7 to 7:1, 1:6 to 6:1, 1:5 to 5:1, 1:4 to 4:1, 1:3 to 3:1, 1:2 to 2:1, or 1:1.

The above values of combined mass concentration may be considered to apply in the context of a "single strength serving" of the sugar-depleted juice product, i.e. a "ready to serve" or "drinkable/edible" product and in particular a sugar-depleted "not from concentrate" juice.

In other embodiments, "sugar-depleted" means that the juice product has been rendered substantially, e.g. essentially, devoid of free glucose and optionally sucrose.

By "substantially devoid of free glucose" it is meant that the sugar-depleted juice product of the invention contains no more than about 5 g/l free glucose, e.g. no more than about 4, 3, 2, 1, 0.5, 0.1, 0.05, 0.01 g/l free glucose, when said juice product is adjusted in volume with water to give a gluconic acid concentration of about 5 g/l or the specific concentrations disclosed below.

By "substantially devoid of sucrose" it is meant that the sugar-depleted juice product of the invention contains no more than about 5 g/l sucrose, e.g. no more than about 4, 3, 2, 1, 0.5, 0.1, 0.05, 0.01 g/l sucrose, when said juice product is adjusted in volume with water to give a gluconic acid concentration of about 5 g/l or the specific concentrations disclosed below.

By "essentially devoid of free glucose" it is meant that the sugar-depleted juice product of the invention contains a trace amount of free glucose. This may also be expressed as essentially undetectable with standard analytical means, or at the limit of detection with such means. These measures preferably take place when said juice product is adjusted in volume with water to give a gluconic acid concentration of about 5 g/l or the specific concentrations disclosed below. Detection may be by any convenient means, e.g. the Reflectoquant™ system of Merck Millipore™ as disclosed in the Examples.

"Essentially devoid of sucrose" should be interpreted in the same way.

The above values for free glucose and sucrose may be considered to apply in the context of a "single strength serving" of the sugar-depleted juice product, i.e. a "ready to serve" or "drinkable/edible" product and in particular a sugar-depleted "not from concentrate" juice.

The terms "free glucose-depleted" and "sucrose-depleted" should be interpreted consistently with the foregoing.

In certain embodiments a sugar-depleted juice product of the invention may have an increased mass concentration ratio of other sugars, e.g. fructose, to non-saccharide soluble components than the corresponding ratios of a juice product that has been prepared from the same fruit or vegetable in the same way but which is not sugar-depleted.

In other embodiments the sugar-depleted juice product may have also been rendered devoid, or at least have a reduced content or be depleted, of other sugars, e.g. fructose, typically present in the same juice product that has been prepared from the same fruit or vegetable in the same way but which is not sugar-depleted. The above embodiments relating to free glucose and/or sucrose can be applied mutatis mutandis in the context of the depletion of other sugars, e.g. fructose.

Therefore, in a further embodiment of the present invention there is provided a sugar-depleted fruit or vegetable juice product, wherein said juice product is a fruit or vegetable juice or juice-retaining fruit or vegetable derived matter, and wherein said juice product is substantially, e.g. essentially, devoid of free glucose and sucrose, said juice product contains at least about 5 g/l gluconic acid and said juice product contains any two or three, of
   (i) at least about 0.5 g/l $Ca^{2+}$,
   (ii) at least about 1 g/l $K^{30}$, and
   (iii) at least about 0.1 g/l $Mg^{2+}$.

In preferred embodiments the sugar-depleted juice product contains at least 6 g/l, e.g. at least about 8, 10, 12, 14, 16, 18, 20, 22, 24, 26, 28, 30, 32, 34, 36, 38, 40, 45, 50, 55, 60, 65, 70, 75 or 80 g/l gluconic acid.

In preferred embodiments the sugar-depleted juice product may contain at least about 0.5 g/l $Ca^{2+}$, e.g. at least about 0.6, 0.7, 0.8, 0.9, 1, 1.5, 2, 2.5, 3, 3.5, 4, 4.5 or 5 g/l $Ca^{2+}$.

In preferred embodiments the sugar-depleted juice product may contain at least about 1 g/l $K^+$, e.g. at least about 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5 or 15 g/l $K^+$.

In preferred embodiments the sugar-depleted juice product may contain at least about 0.1 g/l $Mg^{2+}$, e.g. at least about 0.2, 0.3, 0.4, 0.5, 0.6, 0.7, 0.8, 0.9, or 1 g/l $Mg^{2+}$.

All ratios of $Ca^{2+}$, $K^+$ and/or $Mg^{2+}$ mass concentrations which may be formed from the above values are expressly contemplated.

In certain embodiments the sugar-depleted juice product contains $Ca^{2+}$ and $K^+$ at the above described concentrations. In other embodiments the selected metal ions are $Ca^{2+}$ and $Mg^{2+}$, $Mg^{2+}$ and $K^+$, or $Ca^{2+}$, $K^+$ and $Mg^{2+}$ all at the above described concentrations.

In certain embodiments the juice product of the invention comprises any two or three of $Ca^{2+}$, $K^+$ and $Mg^{2+}$ at mass concentrations which, when said juice product is adjusted in volume with water to give a gluconic acid concentration of about 5 g/l, or the specific concentrations disclosed above, gives the above recited values.

The concentration of metal ions referred to herein are concentrations as may be determined by the physiochemical pressure digestion method described in EN 13805 (2013). Should alternative approaches be used to measure the concentration of metal ions in the juice product, an acid (e.g. nitric acid) digestion step, equivalent to that of EN 13805, must be incorporated immediately prior to analysis.

In further preferred embodiments the sugar-depleted juice product is a palatable ("drinkable" or "edible", "ready to serve", "single strength") juice product, e.g. a juice replacement beverage, that has the same or substantially the same taste and flavour profile and mouth-feel as an unmodified juice product from the same fruit or vegetable. Such a product may be obtained by diluting with water a sugar-depleted juice product of the invention that is more concentrated (contains less water) than the palatable form. It is also preferred that the sugar-depleted juice product is a sugar-depleted "not from concentrate" juice.

A suitably dilute juice that is palatable to the average consumer maybe a juice that corresponds to that obtained directly from the fruit or vegetable in question by a method comprising at least one mechanical means of juice extraction as defined herein. Conveniently this may be expressed as a sugar-depleted juice having a Brix level (soluble solids content) within 30%, e.g. within 25%, 20%, 15%, 10% or 5% of that of juice obtained directly from the fruit or vegetable in question by a method comprising at least one mechanical means of juice extraction as defined herein. The skilled person would be aware that in the context of the present invention the Brix value for a sugar-depleted juice of the invention is a value representing the sum of sugars including gluconic acid.

The CODEX General Standard For Fruit Juices And Nectars (CODEX STAN 247-2005) is incorporated by reference in this regard as a resource for Brix (soluble solids content) thresholds for palatable concentrations of common juices and methodology to calculate the same.

In these embodiments gluconic acid will typically be present in the sugar-depleted juice product at a mass concentration of about 5 to about 100 g/l, e.g. about any one of 10, 15, 20, 25, 30, 32, 34, 36, 38, 40, 42, 44, 46, 48, 50, 52, 54, 56, 60, 65, 70, 75, 80, 85, 90, or 95 to about 100g/l, preferably about any one of 15, 20, 25, 30, 32, 34, 36, 38, 40, 42, 44, 46, 48, 50, 52, 54, 56, 60, 65, 70, 75, 80 or 85 to about 90 g/l, more preferably about any one of 20, 25, 30, 32, 34, 36, 38, 40, 42, 44, 46, 48, 50, 52, 54, 56, 60, 65 or 70 to about 80 g/l, and still more about preferably about any one of 25, 30, 32, 34, 36, 38, 40, 42, 44, 46, 48, 50, 52, 54, 56, 58 or 60 to about 75 g/l.

Any range which may be formed from any of the above recited mass concentrations is expressly contemplated.

In other embodiments gluconic acid will typically be present in the sugar-depleted juice product at a mass concentration of about 10 to about 70 g/l, e.g. about any one of 15, 20, 25, 30, 32, 34, 36, 38, 40, 42, 44, 46, 48, 50, 52, 54, 56, 60, 65 g/l to about 70g/l, preferably about any one of 20, 25, 30, 32, 34, 36, 38, 40, 42, 44, 46, 48, 50, 52, 54, 56 or 60 to about 65 g/l, more preferably about any one of 25, 30, 32, 34, 36, 38, 40, 42, 44, 46, 48, 50, 52, 54 or 56 to about 60 g/l, and still more preferably about any one of 30, 32, 34, 36, 38, 40, 42, 44, 46, 48, 50, 52, 54 or 56 to about 60 g/l.

Any range which may be formed from any of the above recited mass concentrations is expressly contemplated.

Gluconic acid content may be measured by any convenient means, e.g. via an appropriate enzymatic assay (e.g. as supplied by R-Biopharm™) or chromatography based techniques. Such measurements should take into account all forms of gluconic acid, i.e. the free acid, salts thereof and the lactone forms thereof, e.g. D-gluconic acid δ-lactone and D-gluconic acid γ-lactone.

As detailed later, because the preferred method of producing the sugar-depleted juice product of the invention is based on the conversion of at least a portion of the free glucose and optionally the glucose in the sucrose present in a natural juice product to gluconic acid, the exact amount of gluconic acid present in these embodiments will be to an extent dictated by the amounts of free glucose and glucose in sucrose converted to gluconic acid. Ultimately the amount of gluconic acid present in these embodiments will be dictated by the total free glucose and sucrose content of the corresponding natural juice product. As also detailed later, in other embodiments the free fructose and, optionally, fructose in the sucrose in a natural fruit juice product may be converted to glucose and thereby contribute to the amount of gluconic acid in the sugar-depleted juice.

In some instances it might be necessary to add gluconic acid to the sugar-depleted juice product to reach the concentrations required by the invention if the amount of free glucose and the glucose in sucrose available is not sufficiently high or if the intended reduction in glucose and sucrose levels is not sufficiently great.

In these embodiments the sugar-depleted juice product may contain about 0.5 to about 10 g/l $Ca^{2+}$, e.g. about any one of 0.5, 1, 1.5, 2, 2.5, 3, 3.5, 4, 4.5 or 5 to about any one of 5.5, 6, 6.5, 7, 7.5, 8, 8.5, 9 or 9.5 g/l $Ca^{2+}$, preferably about any one of 0.5, 1, 1.5, 2, 2.5, 3, 3.5, or 4 to about any one of 4.5, 5, 5.5, 6, 6.5, 7, 7.5 or 8 g/l $Ca^{2+}$, more preferably about any one of 0.5, 1, 1.5, 2, 2.5 or 3, to about any one of 3.5, 4, 4.5, 5, 5.5 or 6 g/l $Ca^{2+}$, and still more preferably about any one of 0.5, 1, 1.5, 2 or 2.5 to about any one of 3, 3.5, 4, 4.5 or 5 g/l $Ca^{2+}$. Any range which may be formed from any of the above recited mass concentrations is expressly contemplated.

In these embodiments the sugar-depleted juice may contain about 1 to about 20 g/l $K^+$, e.g. about any one of 1, 2, 3, 4, 5, 6, 7, 8, 9 or 10 to about any one of 11, 12, 13, 14, 15, 16, 17, 18, 19 or 20 g/l $K^+$, preferably about any one of 1, 2, 3, 4, 5, 6, 7 or 8 to about any one of 9, 10, 11, 12, 13, 14, 15 or 16 g/l $K^+$, more preferably about any one of 1, 2, 3, 4, 5, or 6 to about any one of 7, 8, 9, 10 11 or 12 g/l $K^+$, and still more preferably about any one of 1, 2, 3, 4, or 5 to about any one of 6, 7, 8, 9 or 10 g/l $K^+$. Any range which may be formed from any of the above recited mass concentrations is expressly contemplated.

In these embodiments the sugar-depleted juice may contain about 0.1 to about 2 g/l $Mg^{2+}$, e.g. about any one of 0.1, 0.2, 0.3, 0.4, 0.5, 0.6, 0.7, 0.8, 0.9 or 1 to about any one of 1.1, 1.2, 1.3, 1.4, 1.5, 1.6, 1.7, 1.8, 1.9 or 2 g/l $Mg^{2+}$, preferably about any one of 0.1, 0.2, 0.3, 0.4, 0.5, 0.6, 0.7 or 0.8 to about any one of 0.9, 1, 1.1, 1.2, 1.3, 1.4, 1.5 or 1.6 g/l $Mg^{2+}$, more preferably about any one of 0.1, 0.2, 0.3, 0.4, 0.5 or 0.6 to about any one of 0.7, 0.8, 0.9, 1 1.1 or 1.2 g/l $Mg^{2+}$, and still more preferably about any one of 0.1, 0.2, 0.3, 0.4 or 0.5, to about any one of 0.6, 0.7, 0.8, 0.9 or 1 g/l $Mg^{2+}$. Any range which may be formed from any of the above recited mass concentrations is expressly contemplated.

All ratios of $Ca^{2+}$, $K^+$ and/or $Mg^{2+}$ mass concentrations which may be formed from the above values are expressly contemplated.

In these embodiments the sugar-depleted juice product has a pH of equal to or greater than about 3 and equal to or less than about 5, e.g. about 3 to about 5, about 3.5 to about 4.8, about 3.6 to about 4.6, about 3.8 to about 4.4, about 3.8 to about 4.6, about 3.9 to about 4.5 or about 4.0 to about 4.5.

Thus, the present invention provides a sugar-depleted fruit or vegetable juice product, wherein said juice product is a fruit or vegetable juice or juice-retaining fruit or vegetable derived matter, preferably wherein said juice product is substantially, e.g. essentially, devoid of glucose and sucrose, wherein said juice product contains at least about 5 g/l gluconic acid and wherein said juice product contains any two or three, of $Ca^{2+}$, $K^+$, and $Mg^{2+}$ at a mass concentration which, when said juice product is adjusted in volume with water to give a gluconic acid concentration of about 5 g/l or the specific concentrations described above, gives:

(i) a mass concentration of $Ca^{2+}$ of about 0.5 to about 10 g/l (ii) a mass concentration of $K^+$ of about 1 to about 20 g/l, (iii) a mass concentration of $Mg^{2+}$ of about 0.1 to about 2 g/l.

The above embodiments may be considered to apply in the context of a "single strength serving" of the sugar-depleted juice product, i.e. a "ready to serve" or "drinkable/edible" product. Preferably the juice product is a sugar-depleted fruit or vegetable juice, in particular a sugar-depleted "not from concentrate" juice.

The above disclosed ranges of $Ca^{2+}$, $K^+$, and $Mg^{2+}$ mass concentrations and pH apply mutatis mutandis to this aspect of the invention.

In other embodiments the above recited values and ranges for $Ca^{2+}$, $K^+$, and $Mg^{2+}$ mass concentrations are the amounts by which $Ca^{2+}$, $K^+$, and $Mg^{2+}$ mass concentrations are increased relative to those present naturally in a juice product which has been prepared from the same fruit or vegetable in the same way. In other words the above recited values and ranges for $Ca^{2+}$, $K^+$, and $Mg^{2+}$ mass concentrations reflect the amounts of $Ca^{2+}$, $K^+$, and $Mg^{2+}$ which have been added or introduced to the juice product or by which the juice product has been supplemented.

Thus in certain embodiments the invention provides provided a sugar-depleted fruit or vegetable juice product, wherein said juice product is a fruit or vegetable juice or juice-retaining fruit or vegetable derived matter, wherein said juice product contains at least about 5 g/l gluconic acid and wherein the mass concentrations of any two or three of $Ca^{2+}$, $K^+$, and $Mg^{2+}$ are increased by (i) at least about 0.5 g/l for $Ca^{2+}$, (ii) at least about 1 g/l for $K^+$, and (iii) at least about 0.1 g/l for $Mg^{2+}$, as compared to the mass concentrations of $Ca^{2+}$, $K^+$, and $Mg^{2+}$ respectively present naturally in a juice product which has been prepared from the same fruit or vegetable in the same way.

Any specific embodiments of individual elements of the above embodiment apply mutatis mutandis to this aspect of the invention.

In other embodiments the juice product of the invention may have a $Ca^{2+}$ mass concentration which is relative to the mass concentration of $Ca^{2+}$ present naturally in a juice product which has been prepared from the same fruit or vegetable in the same way or in the fruit or vegetable from which the juice product is obtained. In these embodiments a natural $Ca^{2+}$ mass concentration of 0 g/l to less than 0.5g/l in a juice product which has been prepared from the same fruit or vegetable in the same way or in the fruit or vegetable from which the juice product is obtained will result in the juice product of the invention having at least about 0.5 g/l $Ca^{2+}$. A natural $Ca^{2+}$ mass concentration of 0.5 g/l to less than 1 g/l will result in the juice product of the invention having at least about 1 g/l $Ca^{2+}$. A natural $Ca^{2+}$ mass concentration of 1 g/l to less than 1.5 g/l will result in the juice product of the invention having at least about 1.5 g/l $Ca^{2+}$. A natural $Ca^{2+}$ mass concentration of 1.5 g/l to less than 2 g/l will result in the juice product of the invention having at least about 2 g/l $Ca^{2+}$. A natural $Ca^{2+}$ mass concentration of 2 g/l to less than 2.5 g/l will result in the juice product of the invention having at least about 2.5 g/l $Ca^{2+}$. A natural $Ca^{2+}$ mass concentration of 2.5 g/l to less than 3 g/l will result in the juice product of the invention having at least about 3 g/l $Ca^{2+}$. A natural $Ca^{2+}$ mass concentration of 3 g/l to less than 3.5 g/l will result in the juice product of the invention having at least about 3.5 g/l $Ca^{2+}$. A natural $Ca^{2+}$ mass concentration of 3.5 g/l to less than 4 g/l will result in the juice product of the invention having at least about 4 g/l $Ca^{2+}$.

In other embodiments the juice product of the invention may have a $K^+$ mass concentration which is relative to the mass concentration of $K^+$ present naturally in a juice product which has been prepared from the same fruit or vegetable in the same way or in the fruit or vegetable from which the juice product is obtained. In these embodiments a natural $K^+$ mass concentration of 0 g/l to less than 1 g/l in a juice product which has been prepared from the same fruit or vegetable in the same way or in the fruit or vegetable from which the juice product is obtained will result in the juice product of the invention having at least about 1 g/l $K^+$. A natural $K^+$ mass concentration of 1 g/l to less than 1.5 g/l will result in the juice product of the invention having at least about 1.5 g/l $K^+$. A natural $K^+$ mass concentration of 1.5 g/l to less than 2 g/l will result in the juice product of the invention having at least about 2 g/l $K^+$. A natural $K^+$ mass concentration of 2 g/l to less than 2.5 g/l will result in the juice product of the invention having at least about 2.5 g/l $K^+$. A natural $K^+$ mass concentration of 2.5 g/l to less than 3 g/l will result in the juice product of the invention having at least about 3 g/l $K^+$. A natural $K^+$ mass concentration of 3 g/l to less than 3.5 g/l will result in the juice product of the invention having at least about 3.5 g/l $K^+$. A natural $K^+$ mass concentration of 3.5 g/l to less than 4 g/l will result in the juice product of the invention having at least about 4 g/l $K^+$. A natural $K^+$ mass concentration of 4 g/l to less than 4.5 g/l will result in the juice product of the invention having at least about 4.5 g/l $K^+$. A natural $K^+$ mass concentration of 4.5 g/l to less than 5 g/l will result in the juice product of the invention having at least about 5 g/l $K^+$.

In other embodiments the juice product of the invention may have a $Mg^{2+}$ mass concentration which is relative to the mass concentration of $Mg^{2+}$ present naturally in a juice product which has been prepared from the same fruit or vegetable in the same way or in the fruit or vegetable from which the juice product is obtained. In these embodiments a natural $Mg^+$ mass concentration of 0 g/l to less than 0.1 g/l in a juice product which has been prepared from the same fruit or vegetable in the same way or in the fruit or vegetable from which the juice product is obtained will result in the juice product of the invention having at least about 0.1 g/l $Mg^{2+}$. A natural $Mg^{2+}$ mass concentration of 0.1 g/l to less than 0.15 g/l will result in the juice product of the invention having at least about 0.15 g/l $Mg^+$. A natural $Mg^{2+}$ mass concentration of 0.15 g/l to less than 0.2 g/l will result in the juice product of the invention having at least about 0.2 g/l $Mg^{2+}$. A natural $Mg^+$ mass concentration of 0.2 g/l to less than 0.25 g/l will result in the juice product of the invention having at least about 0.25 g/l $Mg^{2+}$. A natural $Mg^{2+}$ mass concentration of 0.25 g/l to less than 0.3 g/l will result in the juice product of the invention having at least about 0.3 g/l $Mg^{2+}$. A natural $Mg^{2+}$ mass concentration of 0.3 g/l to less than 0.35 g/l will result in the juice product of the invention having at least about 0.35 g/l $Mg^{2+}$. A natural $Mg^{2+}$ mass concentration of 0.35 g/l to less than 0.4 g/l will result in the juice product of the invention having at least about 0.4 g/l $Mg^{2+}$. A natural $Mg^{2+}$ mass concentration of 0.4 g/l to less than 0.45 g/l will result in the juice product of the invention having at least about 0.45 g/l $Mg^{2+}$. A natural $Mg^{2+}$ mass concentration of 0.45 g/l to less than 0.5 g/l will result in the juice product of the invention having at least about 0.5 g/l $Mg^{2+}$.

The $Ca^{2+}$, $K^+$, and $Mg^{2+}$ mass concentrations present naturally in a juice product which has been prepared from the same fruit or vegetable in the same way, or in the fruit or vegetable from which the juice product is obtained, can be easily determined as described herein. In addition, databases of food composition, e.g. the McCance and Widdowson's Composition of Foods Integrated Dataset of Public Health England and the United States Department of Agriculture Agricultural Research Service National Nutrient Database for Standard Reference, the contents of which are incorporated in their entirety by reference, may be consulted.

Any specific embodiments of individual elements of the invention apply mutatis mutandis to this aspect of the invention.

In a further embodiment there is provided a sugar-depleted fruit or vegetable juice product, wherein said juice product is a fruit or vegetable juice or juice-retaining fruit or vegetable derived matter and wherein at least 75%, 80%, 85%, 90%, 95% or essentially all of said juice or juice-retaining matter is derived from orange, wherein said juice product contains at least about 5 g/l gluconic acid and said juice product contains any two or three, of
  (i) at least about 0.5 g/l $Ca^{2+}$,
  (ii) at least about 2.5 g/l $K^+$, and
  (iii) at least about 0.15 g/l $Mg^{2+}$.

In a further embodiment there is provided a sugar-depleted fruit or vegetable juice product, wherein said juice product is a fruit or vegetable juice or juice-retaining fruit or vegetable derived matter and wherein at least 75%, 80%, 85%, 90%, 95% or essentially all of said juice or juice-retaining matter is derived from apple, wherein said juice product contains at least about 5 g/l gluconic acid and said juice product contains any two or three, of
  (i) at least about 0.5 g/l $Ca^{2+}$,
  (ii) at least about 1.5 g/l $K^+$, and
  (iii) at least about 0.1 g/l $Mg^{2+}$.

In a further embodiment there is provided a sugar-depleted fruit or vegetable juice product, wherein said juice product is a fruit or vegetable juice or juice-retaining fruit or vegetable derived matter and wherein at least 75%, 80%, 85%, 90%, 95% or essentially all of said juice or juice-retaining matter is derived from grape, wherein said juice product contains at least about 5 g/l gluconic acid and said juice product contains any two or three, of
  (i) at least about 0.5 g/l $Ca^{2+}$,
  (ii) at least about 1.5 g/l $K^+$, and
  (iii) at least about 0.15 g/l $Mg^{2+}$.

In a further embodiment there is provided a sugar-depleted fruit or vegetable juice product, wherein said juice product is a fruit or vegetable juice or juice-retaining fruit or vegetable derived matter and wherein at least 75%, 80%, 85%, 90%, 95% or essentially all of said juice or juice-retaining matter is derived from grapefruit, wherein said juice product contains at least about 5 g/l gluconic acid and said juice product contains any two or three, of
  (i) at least about 0.5 g/l $Ca^{2+}$,
  (ii) at least about 2 g/l $K^+$, and
  (iii) at least about 0.15 g/l $Mg^{2+}$.

In a further embodiment there is provided a sugar-depleted fruit or vegetable juice product, wherein said juice product is a fruit or vegetable juice or juice-retaining fruit or vegetable derived matter and wherein at least 75%, 80%, 85%, 90%, 95% or essentially all of said juice or juice-retaining matter is derived from tomato, wherein said juice product contains at least about 5 g/l gluconic acid and said juice product contains any two or three, of
(i) at least about 0.5 g/l $Ca^{2+}$,
(ii) at least about 2.5 g/l $K^+$, and
(iii) at least about 0.15 g/l $Mg^{2+}$.

In a further embodiment there is provided a sugar-depleted fruit or vegetable juice product, wherein said juice product is a fruit or vegetable juice or juice-retaining fruit or vegetable derived matter and wherein at least 75%, 80%, 85%, 90%, 95% or essentially all of said juice or juice-retaining matter is derived from pineapple, wherein said juice product contains at least about 5 g/l gluconic acid and said juice product contains any two or three, of
(i) at least about 0.5 g/l $Ca^{2+}$,
(ii) at least about 1.5 g/l $K^+$, and
(iii) at least about 0.15 g/l $Mg^{2+}$.

In a further embodiment there is provided a sugar-depleted fruit or vegetable juice product, wherein said juice product is a fruit or vegetable juice or juice-retaining fruit or vegetable derived matter and wherein at least 75%, 80%, 85%, 90%, 95% or essentially all of said juice or juice-retaining matter is derived from cranberry, wherein said juice product contains at least about 5 g/l gluconic acid and said juice product contains any two or three, of
(i) at least about 0.5 g/l $Ca^{2+}$,
(ii) at least about 1 g/l $K^+$, and
(iii) at least about 0.1 g/l $Mg^{2+}$.

In a further embodiment there is provided a sugar-depleted fruit or vegetable juice product, wherein said juice product is a fruit or vegetable juice or juice-retaining fruit or vegetable derived matter and wherein at least 75%, 80%, 85%, 90%, 95% or essentially all of said juice or juice-retaining matter is derived from carrot, wherein said juice product contains at least about 5 g/l gluconic acid and said juice product contains any two or three, of
(i) at least about 0.5 g/l $Ca^{2+}$,
(ii) at least about 3 g/l $K^+$, and
(iii) at least about 0.15 g/l $Mg^{2+}$.

Any specific embodiments of individual elements of the invention described above apply mutatis mutandis to this aspect of the invention, in particular the specific values and ranges for $Ca^{2+}$, $K^+$ and $Mg^{2+}$ mass concentrations. In certain embodiments the above specific juice products of the invention comprises any two or three of $Ca^{2+}$, $K^+$ and $Mg^{2+}$ at mass concentrations which, when said juice product is adjusted in volume with water to give a gluconic acid concentration of about 5 g/l, or the specific concentrations disclosed above, gives the above recited values.

The precise combination of metal ion concentrations in any particular embodiment will be to an extent dictated by the overall composition of the juice product that has been sugar-depleted in accordance with the invention. For instance, a juice product from a citrus fruit might require a different combination of metal ion concentration to that required by a juice product from carrots. The skilled person would also appreciate that adjustment and optimisation may be required to allow for natural variations between juice product batches on account of differences in the source of the fruit/vegetables, the overall ripeness of the fruit and the varieties of fruit used to prepare the juice product. In the present invention it is assumed that the sensory properties of the sugar-depleted juice product are essentially equivalent to a juice product obtained from adequately ripe fruit/vegetables, i.e. fruit and vegetables that if juiced would give rise to a palatable beverage. The skilled person would be easily able to determine workable and optimal combinations of metal ion concentrations for his particular juice product of interest in accordance with the invention, i.e. those that give rise to a sugar-depleted juice product that is highly palatable and which retains sufficiently the flavour and mouth-feel of the unmodified juice product. Routine techniques such as the use of trained sensory assessors can be employed in this regard.

The sugar-depleted juice products of the present invention may be prepared through one or more enzyme treatments and metal ion supplementation. Specifically, a treatment with an enzyme that converts glucose into gluconic acid (e.g. glucose oxidase), an optional treatment with an enzyme which hydrolyses sucrose to glucose and fructose (e.g. invertase) and supplementation with one or more, preferably any two or three, of a source of $Ca^{2+}$, a source of $Mg^{2+}$ and a source of $K^+$ in amounts sufficient to reach the amounts $Ca^{2+}$, $Mg^{2+}$ and $K^+$ required by the sugar-depleted juice product of the invention. Preferably the sugar-depleted juice products of the present invention are not prepared by a method comprising a step in which the juice product is contacted with a glucose-fructose oxidoreductase, e.g. the glucose-fructose oxidoreductase from *Zymomonas mobilis*. In such embodiments the sugar-depleted juice products of the present invention comprise sorbitol in the same amounts or less than those in the same juice product that has been prepared from the same fruit or vegetable in the same way but which is not sugar-depleted.

In other embodiments the sugar-depleted juice product of the invention is also substantially, e.g. essentially, devoid of fructose, which term is to be interpreted as discussed above for glucose and sucrose. This may be conveniently achieved by further treating the sugar-depleted juice product of the invention with an enzyme capable of converting fructose into a derivative form, preferably a derivative form with a lower calorific value and/or more favourable glycaemic profile. Such enzymes may include 5-D-fructose dehydrogenase (e.g. as described in US 2009/0214620). Alternatively, fructose may be enzymatically converted to glucose prior to or concurrent with treatment with glucose oxidase. Such enzymes may be defined as glucose isomerases and include glucose-6-phosphate isomerase and D-xylose isomerase (e.g. as described in US 2009/0311232). In these embodiments in may be necessary to supplement the sugar-depleted juice product with a sweetening agent, e.g. an artificial sweetening agent that is not a sugar (e.g. stevia, sucralose and aspartame).

In certain embodiments the sugar-depleted juice product of the invention does not contain detectable amounts of active glucose oxidase, and/or invertase and/or 5-D-fructose dehydrogenase and/or a glucose isomerase (e.g. glucose-6-phosphate isomerase or D-xylose isomerase). Expressed numerically the sugar-depleted juice product of the invention displays enzyme activities for the above enzymes of no more than 1 U/ml, e.g. no more than 0.1 U/ml, 0.05 U/ml or 0.01 U/ml. Nevertheless, the juice product of the invention may still comprise inactivated, e.g. denatured, forms of one or more of the above-mentioned enzymes, e.g. glucose oxidase and/or invertase. In certain embodiments the sugar-depleted juice product of the invention does not contain detectable amounts of a glucose-fructose oxidoreductase, e.g. the glucose-fructose oxidoreductase from *Zymomonas mobilis*, whether active, inactive, denatured or otherwise.

The sugar-depleted juice product of the invention may be supplemented with other compounds to enhance the palatability of the product, e.g. by enhancing taste, flavour and mouth-feel. Such compounds include, but are not limited to other metal ions (e.g. $Na^+$, $Fe^{2+}$, $Fe^{3+}$), vitamins (e.g. vitamins A, B, C, D, E, K and subtypes thereof), minerals (e.g. compounds containing phosphorous, sulphur, fluorine, chlorine, boron, chromium, cobalt, copper, iron, manganese, molybdenum, selenium, silicon, tin, vanadium and zinc), flavourings (natural and artificial), flavour enhancers (e.g. monosodium glutamate), preservatives, artificial sweeteners (e.g. stevia, sucralose and aspartame), polyphenols, organic acids (other than gluconic acid), acidity regulators and stabilisers. However, in other embodiments the sugar-depleted juice product of the invention does not contain the above classes of additives in quantities greater than those found naturally in the unmodified juice product.

In preferred embodiments the sugar-depleted juice product of the invention contains only the sodium present naturally in the unmodified juice product. Expressed numerically, in preferred embodiments the sugar-depleted juice product of the invention contains $Na^+$ at a mass concentration which, when said juice product is adjusted in volume with water to give a gluconic acid concentration of about 5 g/l, or the specific concentrations disclosed above, gives a mass concentration of $Na^+$ of no more than about 0.5 g/l, e.g. no more than about 0.45, 0.40, 0.35, 0.30, 0.25 or 0.20 g/l.

The term "fruit" is used herein in its culinary sense; that is to encompass any sweet, edible part of a plant, even if it does not develop from a floral ovary, that has a liquid part that may be extracted by mechanical means and which is safely edible by a human. For the purposes of the invention, this does not include nuts and grains. For the purposes of the invention this does include tomato. Industrially relevant examples include but are not limited to the pome fruits (e.g. apple, pear, rosehip, medlar, quince); the citrus fruits (e.g. orange, blood orange, grapefruit, tangerine, clementine, mandarin, lemon, lime, kumquat, pomelo); the Rubus fruits (e.g. raspberry, blackberry, dewberry, boysenberry, olallieberry, tayberry, cloudberry, loganberry, salmonberry, thimbleberry, wineberry); the Ribes fruits (e.g. blackcurrant, redcurrant, white currant, gooseberry); the Ericaceae fruits (e.g. blueberry, bilberry, cranberry, bearberry, crowberry, falberry, huckleberry, lingonberry); the *Prunus* stone fruits (e.g. peach, plum, nectarine, apricot, greengage, cherry, damson); grapes, pomegranate, fig, passion fruit, guava, mango, melon, pineapple, elderberry, rhubarb, soursop, tamarind, strawberry, kiwifruit, lychee, papaya, banana, advocado and tomato.

The term "vegetable" is used herein in its culinary sense; that is to encompass any savoury, edible part of a plant, even if it does develop from a floral ovary, that has a liquid part that may be extracted by mechanical means and which is safely edible by a human. Industrially relevant examples include but are not limited to leaf vegetables (e.g. spinach, wheatgrass, choi, lettuce, cabbage, kale, cress, chard); root vegetables (e.g. carrot, parsnip, potato, yam, beetroot, burdock, ginger, galangal, Jerusalem artichoke, turnip, radish); bulb and stem vegetables (e.g. onion, garlic, asparagus, leek, fennel, celery, lemongrass); and podded vegetables (pea, runner bean, green bean, broad bean). Carrot, wheatgrass, celery, beetroot, ginger and spinach are of note.

The sugar-depleted juice product may be a mixture of juice products from different fruits and/or vegetables. Said juice products may be blended once each has been rendered sugar-depleted or may be blended in their natural sugar-complete state and subsequently rendered sugar-depleted.

Preferably the juice product is a fruit juice product or a mixture of fruit juice products selected from apple, pear, orange, grapefruit, mandarin, tangerine, clementine, lemon, lime, grape, pineapple, mango, guava, soursop, tomato, pomegranate, cranberry, blueberry, blackcurrant, passion fruit, rhubarb, melon, strawberry, raspberry, peach, nectarine, apricot and cherry.

As mentioned above, the sugar-depleted juice product of the present invention may be prepared through one or more enzyme treatments and metal ion supplementation. Specifically, an enzyme treatment that converts glucose into gluconic acid (e.g. glucose oxidase), an optional treatment with an enzyme which hydrolyses sucrose to glucose and fructose (e.g. invertase) and supplementation with one or more, preferably any two or three, of a source of $Ca^{2+}$, a source of $Mg^{2+}$ and a source of $K^+$ in amounts sufficient to reach the amounts $Ca^{2+}$, $Mg^{2+}$ and $K^+$ required by the sugar-depleted juice product of the invention. The juice product undergoing the treatments of the invention may be in concentrated form or diluted form. In other embodiments the sugar-depleted juice product that has been prepared in accordance with the invention may undergo concentration or dilution. In still further embodiments, concentration and/or dilution steps may interspace the treatment steps of the invention.

Thus, in another aspect of the invention, there is provided a method for the preparation of a sugar-depleted fruit or vegetable juice product, wherein said sugar-depleted juice product is a fruit or vegetable juice or juice-retaining fruit or vegetable derived matter, wherein said sugar-depleted juice product contains at least about 5 g/l gluconic acid and wherein said sugar-depleted juice product contains any two or three, of
 (i) at least about 0.5 g/l $Ca^{2+}$,
 (ii) at least about 1 g/l $K^+$, and
 (iii) at least about 0.1 g/l $Mg^{2+}$,
i.e. any of the sugar-depleted juice products disclosed herein, said method comprising providing a fruit or vegetable juice product containing free glucose and/or sucrose and:
 (a) contacting said juice product with an enzyme which hydrolyses sucrose to glucose and fructose,
 (b) contacting the enzyme treated juice product of step (a) with an enzyme which converts glucose into gluconic acid, and
 (c) supplementing said juice product with one or more, preferably any two or three, of a source of $Ca^{2+}$, a source of $Mg^{2+}$ and a source of $K^+$ in an amount sufficient to give said mass concentrations of $Ca^{2+}$, $Mg^{2+}$ and/or $K^+$, respectively,
wherein steps (a) and/or (b) may be performed simultaneously with step (c) or before or after step (c).

In other embodiments said method comprises providing a sucrose-depleted fruit or vegetable juice product containing free glucose and:
 (d) contacting said juice product with an enzyme which converts glucose into gluconic acid, and
 (e) supplementing said juice product with one or more, preferably any two or three, of a source of $Ca^{2+}$, a source of $Mg^{2+}$ and a source of $K^+$ in an amount sufficient to give said mass concentrations of $Ca^{2+}$, $Mg^{2+}$ and/or $K^+$, respectively,
wherein steps (d) and (e) may be performed simultaneously or separately in any order.

In other embodiments said method comprises providing a sucrose-depleted fruit or vegetable juice product containing free glucose and said mass concentrations of any two or three of $Ca^{2+}$, $Mg^{2+}$ and/or $K^+$, respectively and:
 (f) contacting said juice with an enzyme which converts glucose into gluconic acid.

In other embodiments said method comprises providing a free glucose-depleted fruit or vegetable juice product, wherein said juice product contains at least about 5 g/l gluconic acid and:
- (g) contacting said juice product with an enzyme which hydrolyses sucrose to glucose and fructose,
- (h) supplementing said juice product with one or more, preferably any two or three, of a source of $Ca^{2+}$, a source of $Mg^{2+}$ and a source of $K^+$ in an amount sufficient to give said mass concentrations of $Ca^{2+}$, $Mg^{2+}$ and/or $K^+$, respectively, wherein steps (g) and (h) may be performed simultaneously or separately in any order.

In other embodiments said method comprises providing a free glucose-depleted fruit or vegetable juice product, wherein said juice product contains at least about 5 g/l gluconic acid and said mass concentrations of any two or three of $Ca^{2+}$, $Mg^{2+}$ and/or $K^+$, respectively and:
- (i) contacting said juice product with an enzyme which hydrolyses sucrose to glucose and fructose.

In other embodiments said method comprises providing a free glucose and optionally sucrose depleted fruit or vegetable juice product, wherein said juice product contains at least about 5 g/l gluconic acid and:
- (j) supplementing said juice product with one or more, preferably any two or three, of a source of $Ca^{2+}$, a source of $Mg^{2+}$ and a source of $K^+$ in an amount sufficient to give said mass concentrations of any two or three of $Ca^{2+}$, $Mg^{2+}$ and/or $K^+$, respectively.

In other embodiments said method comprises providing a fruit or vegetable juice product containing free glucose and/or sucrose and said mass concentrations of any two or three of $Ca^{2+}$, $Mg^{2+}$ and/or $K^+$, respectively, and:
- (k) contacting said juice product with an enzyme which hydrolyses sucrose to glucose and fructose, and
- (l) contacting the enzyme treated juice of step (k) with an enzyme which converts glucose into gluconic acid, wherein steps (k) and (l) may be performed simultaneously or separately.

In other embodiments said method comprises providing a fruit or vegetable juice product containing free glucose and optionally sucrose, and:
- (m) contacting said juice product with an enzyme which converts glucose into gluconic acid, and
- (n) supplementing said juice product with one or more, preferably any two or three, of a source of $Ca^{2+}$, a source of $Mg^{2+}$ and a source of $K^+$ in an amount sufficient to give said mass concentrations of any two or three of $Ca^{2+}$, $Mg^{2+}$ and/or $K^+$, respectively, wherein steps (m) and (n) may be performed simultaneously or separately in any order.

In other embodiments said method comprises providing a fruit or vegetable juice product containing free glucose and optionally sucrose and said mass concentrations of any two or three of $Ca^{2+}$, $Mg^{2+}$ and/or $K^+$, respectively, and:
- (o) contacting said juice product with an enzyme which converts glucose into gluconic acid.

In these embodiments the final step recited therein is sufficient to result in the formation of a sugar-depleted juice product of the invention. However, further processing steps may be included before or following or intervening the recited steps and the final product may still be considered a sugar-depleted juice product of the invention to the extent such products are defined herein.

In these embodiments the term "said juice product" or "the juice product" should be construed according to immediate context and taking into account preceding treatment steps in all possible sequences, unless the term is directly preceded or directly followed by the qualifying term "sugar-depleted", in which case reference is being made to the sugar-depleted juice products of the invention as described herein.

Preferably in these embodiments "depleted" means substantially, e.g. essentially, devoid as defined herein.

Preferably the enzyme which hydrolyses sucrose to glucose and fructose is an invertase or a sucrase (e.g. sucrase-isomaltase and sucrose alpha-glucosidase).

Preferably the enzyme which converts glucose to gluconic acid is a glucose oxidase. Preferably the enzyme which converts glucose to gluconic acid is not a glucose-fructose oxidoreductase, e.g. the glucose-fructose oxidoreductase from *Zymomonas mobilis*.

The step of contacting with the enzyme which hydrolyses sucrose to glucose and fructose is performed for a time and with an amount of enzyme that, under the physical conditions used (e.g. pH, temperature, pressure and oxygen concentration), are sufficient to hydrolyse a sufficient amount of sucrose in the sample to glucose and fructose to render the sample sucrose-depleted. Preferably, the step of contacting with the enzyme which hydrolyses sucrose to glucose and fructose is performed for a time and with an amount of enzyme that, under the physical conditions used, are sufficient to hydrolyse substantially, e.g. essentially, all of the sucrose in the sample to glucose and fructose, i.e. to render the sample substantially, e.g. essentially, devoid of sucrose.

In embodiments in which invertase is selected as the enzyme to hydrolyse sucrose to glucose and fructose, the enzyme will typically be used at a concentration of 500-50000 U/l, preferably 1000-10000 U/l, most preferably at about 5000 U/l, e.g. 4500-5500 U/l and the invertase should be allowed to incubate with the sample for up to 48 hours, preferably 6-48, 6-36, 6-24 or 6-20 hours, most preferably 8-12 hours at a temperature of 5 to 30° C., e.g. 10 to 28° C., 16 to 24° C. or about room temperature (20° C.). Typically, this step of the methods of the invention will be conducted at atmospheric pressure, e.g. about 70 kPa to about 105 kPa. Typically this step of the methods of the invention will be conducted at an acidic to neutral pH, e.g. about 2 to about 8, about 3 to about 7, about 4 to about 6, about 4 to about 5, e.g. around 4.5. These conditions may also be applied generally in the context of the enzyme used to hydrolyse sucrose to glucose and fructose.

The step of contacting with the enzyme which converts glucose to gluconic acid is performed for a time and with an amount of enzyme that, under the physical conditions used (e.g. temperature, pressure and oxygen concentration), are sufficient to convert a sufficient amount of free glucose in the sample to gluconic acid to render the sample glucose-depleted. Preferably, the step of contacting with the enzyme which converts glucose to gluconic acid is performed for a time and with an amount of enzyme that, under the physical conditions used, are sufficient to convert substantially, e.g. essentially, all of the free glucose in the sample to gluconic acid, i.e. to render the sample substantially, e.g. essentially, devoid of free glucose. Preferably the action of the enzyme which converts glucose to gluconic acid (e.g. glucose oxidase) results in the requisite amounts of gluconic acid.

In embodiments in which glucose oxidase is selected as the enzyme to convert glucose to gluconic acid, the enzyme will typically be used at a concentration 300-30000 U/l, more preferably 1000-10000U/l, most preferably at about 3000 U/l, e.g. 2500-3500 U/l and the glucose oxidase should be allowed to incubate with the sample for up to 48 hours, preferably 2-48, 2-36, 2-24, 2-18, 2-12 or 2-10 hours, most preferably 3-4 hours at a temperature of 5 to 30° C., e.g. 10 to 28° C., 16 to 24° C. or about room temperature (20° C.). Typically, this step of the methods of the invention will be conducted at atmospheric pressure, e.g. about 70 kPa to about 105 kPa. These conditions may also be applied generally in the context of the enzyme used to convert glucose to gluconic acid.

The presence of oxygen is necessary for glucose oxidase to effectively convert glucose into gluconic acid. The treatment of certain juices in accordance with the invention may therefore benefit from oxygen supplementation in order to ensure, optimal enzyme activity and/or conversion of sufficient amounts of glucose to gluconic acid. Accordingly, in another preferred embodiment of the present invention, oxygenation is performed at least during the glucose oxidase treatment step. The oxygen may be supplied in the form of air, but pure oxygen ($O_2$) is preferable since the process of enzymatic conversion of glucose to gluconic acid is tends to be faster when pure oxygen is supplied.

The oxygenation of the juice product may result in the oxidation of ascorbic acid (vitamin C). Thus, in these embodiments the fruit juice product of the invention may be substantially, e.g. essentially, devoid of the reduced form of ascorbic acid. By "substantially devoid of ascorbic acid" it is meant that the sugar-depleted juice product of the invention contains no more than about 10 mg/l ascorbic acid, e.g. no more than about 8, 6, 5, 4, 3, 2, 1, 0.5, 0.1, 0.05, 0.01 mg/l ascorbic acid, when said juice product is adjusted in volume with water to give a gluconic acid concentration of about 5 g/l or the specific concentrations disclosed above. By "essentially devoid of ascorbic acid" it is meant that the sugar-depleted juice product of the invention contains a trace amount of ascorbic acid. This may also be expressed as essentially undetectable with standard analytical means, or at the limit of detection with such means. These measures preferably take place when said juice product is adjusted in volume with water to give a gluconic acid concentration of about 5 g/l or the specific concentrations disclosed below. Detection may be by any convenient means, e.g. the Reflectoquant™ system of Merck Millipore™ as disclosed in the Examples. In other embodiments however the juice product contains ascorbic acid, e.g. at a mass concentration about equal to or above that of the unmodified juice product, i.e. the juice product has been supplemented with ascorbic acid e.g. following (or in some embodiments during or after) the oxygenation of the juice product during its production.

A by-product of the conversion of glucose to gluconic acid by glucose oxidase is hydrogen peroxide. Accordingly, in a preferred embodiment catalase or other hydrogen peroxide degrading enzyme is present during any glucose oxidase treatment step or any glucose oxidase treated sample is treated with catalase or other hydrogen peroxide degrading enzyme.

Glucose oxidase performs optimally at about pH 3-6 and as such the step of contacting the juice sample with glucose oxidase will preferably be conducted at about pH 3-6, preferably about 3.4-5, more preferably about 3.6-4.6 or 3.6-4.8 and most preferably about 3.8-4.4. These conditions may also be applied generally in the context of the enzyme used to convert glucose to gluconic acid. The pH range may be controlled by any convenient means, e.g. by the use of appropriate, acids, bases and/or buffers. It may be convenient to adjust pH prior to treatment of the sample with glucose oxidase and/or during the treatment itself, in which case the pH-adjusting agent(s) may be introduced in a plurality of applications. pH may be monitored by any convenient means, e.g. pH meter. In preferred embodiments, pH is controlled, at least in part, with the source of $Ca^{2+}$, $Mg^{2+}$ and/or $K^+$, e.g. hydroxides, oxides or salts of these metals. As shown in the Examples, MgO (e.g. in the form of a slurry, e.g. a slurry wherein the liquid part is an aliquot of the juice undergoing treatment), $Mg(OH_2)$, KOH and $Ca(OH)_2$ (e.g. in solid form, for instance as a powder) may be conveniently used.

The sources of $Ca^{2+}$, $Mg^{2+}$ and/or $K^+$ are only restricted insofar as the sources must be compatible with food products, they do not affect the activities of any enzymes used after their introduction to the juice and they do not have a detrimental effect on the advantageous properties of the sugar-depleted juice product of the invention, i.e. its palatability and its favourable glycaemic profile. The skilled person would have no trouble in selecting appropriate sources of $Ca^{2+}$, $Mg^{2+}$ and/or $K^+$. By way of example, suitable sources include but are not limited to salts (e.g. halide salts, including fluoride, chloride, bromide, iodide salts; organic salts, including acetate, citrate, glutamate), oxides, hydroxides, peroxides, sulphates, phosphates, nitrites, nitrates, bicarbonates and carbonates. Oxides, peroxides and hydroxides are of note as the inventors have found that these compounds, when added to the juice product, do not go on to form compounds which may affect the flavour and mouth-feel of the juice product. For such reasons bicarbonate and carbonate salts of $Ca^{2+}$, $Mg^{2+}$ and/or $K^+$ should be used with some care and preferably will not be used. In certain embodiments calcium carbonate in particular is not used. A plurality of different sources of $Ca^{2+}$, $Mg^{2+}$ and/or $K^+$ may be used, e.g. MgO, $Mg(OH_2)$, KOH, $K_2O_2$, CaO and $Ca(OH)_2$. Conveniently the sources of $Ca^{2+}$, $Mg^{2+}$ and/or $K^+$ may be selected to optimise the enzyme treatment steps. For instance, oxides and hydroxides may be selected if the enzyme treatments would be improved by raising the pH of the reaction mixture. Solid (e.g. powder, granule or pellet) forms of the sources of $Ca^{2+}$, $Mg^{2+}$ and/or $K^+$ may be advantageous as perceptible dilution of the juice product is avoided.

The exact total sugar content of the final sugar-depleted juice product obtained from the methods according to the invention will of course vary with the raw material and the process specifications, but the glucose and optionally the sucrose levels will be reduced, e.g. to trace levels, and the fructose levels may be increased accordingly (if there has been conversion of sucrose to glucose and fructose), but will preferably still be within the possible range for natural variation within different species for the raw material used. The overall sugar levels may be lower, preferably lowered by 0-70%, usually 10-50% depending on raw material, and most preferably by 25-35%.

In other embodiments the sugar-depleted juice product of the invention is also depleted of, e.g. rendered essentially devoid of, free fructose. This may be conveniently achieved by incorporating a step in which the juice product undergoing treatment is exposed to an enzyme capable of converting free fructose into a derivative form, preferably a derivative form with a lower calorific value and/or more favourable glycaemic profile. Such enzymes may include 5-D-fructose dehydrogenase.

In the methods of the invention treatment with said enzyme should preferably occur after, although not necessarily directly after, the step in which sucrose is hydrolysed to glucose and fructose, or treatment with said enzyme is of a sample that is provided depleted of, e.g. devoid of, sucrose and/or glucose.

Alternatively, free fructose may be enzymatically converted to free glucose, e.g. prior to or concurrent with treatment with glucose oxidase. Such enzymes may be define as glucose isomerases and include glucose-6-phosphate isomerase and D-xylose isomerase.

In a further embodiment the starting material for the above described methods is a material that is fructose-depleted, e.g. substantially or essentially devoid of fructose.

Glucose, sucrose, gluconic acid and, if required, fructose may be monitored in the methods of the invention by any of the numerous routine and convenient techniques available to the skilled person. By way of example, the free glucose and the sucrose concentration in juice samples may be measured using a rapid and simple reflectometric based kit (e.g. Reflectoquant from Merck) and free fructose and gluconic acid may be determined via an appropriate enzymatic assay (e.g. as supplied by R-Biopharm).

Any or all of the enzymes used in the methods of the invention may be used in a form immobilised a solid support, preferably a particulate solid support, e.g. a magnetic particulate solid support. In this way recovery of the enzyme(s) is convenient. Preferably, glucose oxidase and/or catalase are used in a form immobilised on a solid support, preferably a solid support carrying both glucose oxidase and catalase immobilised thereon is employed in the methods of the invention.

In certain embodiments the sugar-depleted juice product of the invention does not contain detectable amounts of an active form of one or more the above-mentioned enzymes. This may be achieved by mechanical removal of the enzymes, e.g. by affinity chromatography or by collecting the enzyme linked solid support if such supports are used. Alternatively or additionally the sugar-depleted juice product of the invention may undergo heat treatment to inactivate the enzyme. Conveniently this may take the form of a pasteurisation process. Thus, in certain embodiments, the juice product of the invention may still comprise inactivated forms of one or more of the above-mentioned enzymes, e.g. an enzyme which converts glucose into gluconic acid (e.g. glucose oxidase) and/or an enzyme which hydrolyses sucrose to glucose and fructose (e.g. invertase).

The starting materials for the above described methods may be provided in pasteurised form.

In a further aspect of the invention there is provided a sugar-depleted juice product obtained or obtainable from the methods disclosed herein.

The sugar-depleted juice product of the invention may of course also be used in the preparation of other food products, e.g. purees, sauces and toppings, jams, jellies, fruit butters and spreads, dessert products (including frozen desserts such as ice cream), juice based candies or gelatins, mixed juice products such as smoothies or yoghurts, diabetic, low carbohydrate and low calorie products, or dietary supplements containing juice. The sugar-depleted juice product of the invention may also be used to make alcoholic products such as wine with reduced alcohol content (from grape juice or other juices), either directly from juice product according to the present invention by standard wine making techniques, or by mixing the juice product with alcohol and optionally other ingredients.

The presence of gluconic acid in combination with reduced amounts of sucrose and glucose means the modified juice product of the invention has a glycaemic response, a glycaemic index, a glycaemic load and an insulin response which are significantly lower than those of an untreated juice, i.e. a more favourable glycaemic profile and lower available carbohydrate content, respectively, which in turn reduces the amount of dietary energy provided by the product, and thus renders the modified juice product useful as part of a healthy diet in healthy subjects, and also surprisingly effective in treating subjects with or at risk of developing complex metabolic disorders associated with the over-consumption of glucose and/or sucrose and/or inappropriate metabolism of glucose including metabolic syndrome, diabetes, obesity, dyslipidemia, insulin resistance, hypertension and liver steatosis. The superior palatability of the sugar-depleted juice product of invention means that the product is a viable alternative to natural fruit juice products that will see enthusiastic adoption and prolonged use by consumers, resulting in the above beneficial effects in consumers and patients.

The sugar-depleted juice product of the invention preferably results in a reduced insulin response in a subject as measured by the area under the curve (AUC) of a subject's blood insulin (preferably venous blood insulin) levels over time, preferably over about 15 mins, 30 mins, 45 mins, 60 mins, 75 mins, 90 mins, 105 mins, 120 mins, 150 mins, 180 mins, 210 mins or 240 mins immediately following consumption of the sugar-depleted juice product, relative to a juice product that has been prepared from the same fruit or vegetable in the same way but which is not sugar-depleted. Preferably the AUC is calculated as the incremental AUC (iAUC), i.e. all area below the curve but above the fasting blood insulin concentration. Preferably the AUC, e.g. the iAUC, is calculated over about 120 mins. The insulin response of each product should be determined in the same way.

The sugar-depleted juice product preferably results in an area under the blood insulin curve as defined above in response to its consumption that is no more than 75%, e.g. no more than about 70, 65, 60, 55, 50, 48, 46, 44, 42, 40, 38, 36, 34, 32, 30, 28, 26, 24, 22, 20, 18, 16, 14, 12, 10, 5 or 1% of that of a juice product that has been prepared from the same fruit or vegetable in the same way but which is not sugar-depleted.

The sugar-depleted juice product of the invention preferably results in enhanced postprandial insulin sensitivity, e.g. as measured by ISI according to Belifore (ISI=2/[AUC insulin×AUC glucose+1] relative to a juice product that has been prepared from the same fruit or vegetable in the same way but which is not sugar-depleted. The sugar-depleted juice product preferably results in postprandial insulin sensitivity that is at least 2 times, e.g. 3, 4, 5, 6, 7, 8, 9 or 10 times greater than that of a juice product that has been prepared from the same fruit or vegetable in the same way but which is not sugar-depleted.

Thus, in a further aspect the invention provides a method of assisting in maintaining the health and well-being of a subject or for maintaining or promoting health and well-being in a subject, said method comprising consuming a sugar-depleted juice product of the invention. The use of the juice products of the invention in such methods is contemplated as is the use of the juice products of the invention in the manufacture of a nutraceutical or food-substitute for use in such methods.

Complex metabolic conditions associated with the over-consumption of glucose and/or sucrose and/or inappropriate metabolism of glucose, e.g. metabolic syndrome, diabetes mellitus type II, obesity, dyslipidemia, insulin resistance, hypertension and liver steatosis are well known, however successful treatment thereof has remained elusive. It has now surprisingly been found that simply reducing a subject's dietary intake of these sugars does not effectively treat these conditions but that a more fruitful approach is to provide these subjects with a food-substitute having a more favourable glycaemic profile and/or insulin response and/or the ability to increase insulin sensitivity, specifically a sugar-depleted juice product containing gluconic acid in amounts corresponding to amounts of glucose removed from the juice product, i.e. a sugar-depleted juice product of the invention.

Thus, in a further aspect the invention provides a method for the treatment or prevention of a disease or condition associated with the over-consumption of glucose and/or sucrose and/or inappropriate metabolism of glucose, said method comprising administering a sugar-depleted juice product of the invention to a subject on a calorie-controlled diet.

Expressed differently, the invention provides a sugar-depleted juice product of the invention for use in the treatment or prevention of a disease or condition associated with the over-consumption of glucose and/or sucrose and/or inappropriate metabolism of glucose in a subject on a calorie-controlled diet.

Expressed differently, the invention provides for the use of a sugar-depleted juice product of the invention in the manufacture of a medicinal product for use in the treatment or prevention of a disease or condition associated with the over-consumption of glucose and/or sucrose and/or inappropriate metabolism of glucose in a subject on a calorie-controlled diet.

A calorie-controlled diet is a diet which permits a subject to consume a defined number of calories per day, typically this will be a calorie-restricted diet that permits the subject to consume a number of calories per day that is fewer than the number the subject consumed before adopting the diet. This may be fewer than the number of calories recommended by the skilled practitioner for the average subject or a subject of equivalent body proportions. Preferably the diet will be sugar-controlled/sugar-restricted, in particular will be free glucose- and/or sucrose-controlled/restricted, which terms should be interpreted as for calorie-controlled and calorie restricted.

The disease or condition associated with the over-consumption of glucose and/or sucrose and/or inappropriate metabolism of glucose may be selected from metabolic syndrome, diabetes mellitus type II, obesity, abdominal obesity, dyslipidaemia, insulin resistance, hyperinsulinemia, impaired glucose metabolism, hypertension, liver steatosis, steatohepatitis, hypertriglyceridemia, hypercholesterolemia, low HDL levels, high LDL levels, pancreatitis, neurodegenerative disease, retinopathy, nephropathy and neuropathy. Obesity, abdominal obesity, dyslipidaemia, insulin resistance, hyperinsulinemia, impaired glucose metabolism, hypertension, hypertriglyceridemia, hypercholesterolemia, low HDL levels, high LDL levels, neurodegenerative disease, retinopathy, nephropathy and neuropathy are of note.

Acidification of the sugar-depleted juice and the intestinal milieu by gluconic acid and complex formation with minerals such as calcium, magnesium, potassium, selenium, zinc and iron increases their solubility and bioavailability. This leads to increased absorption and retention of these minerals and consequently the contribution of these minerals to the on-going health and well-being of a subject is maximised. By way of example, calcium plays a role in blood coagulation, energy-yielding metabolism, muscle function, neurotransmission, digestive enzyme function, cell division and differentiation, development and maintenance of bones and teeth; potassium plays a role in muscular and neurological function and blood pressure; magnesium plays a role in the reduction of tiredness and fatigue, electrolyte balance, energy-yielding metabolism, neurotransmission, muscle contraction, protein synthesis, psychological function, maintenance of bones and teeth, cell division; selenium plays a role in spermatogenesis, maintenance of hair and nails, immune system function, thyroid function, protection of DNA, proteins and lipids from oxidative damage; zinc plays a role in DNA synthesis and cell division, carbohydrate and macronutrient metabolism, cognitive function, fertility and reproduction, maintenance of serum testosterone concentrations, vitamin A metabolism, protein synthesis, maintenance of bones, hair, nails and skin, immune system function, protection of DNA, proteins and lipids from oxidative damage, DNA synthesis and cell division, and iron plays a role in cognitive function, energy-yielding metabolism, formation of red blood cells and haemoglobin, oxygen transport, immune system function, reduction of tiredness and fatigue, cell division and cognitive development of children. The specific levels of $Ca^{2+}$, $K^+$ and $Mg^{2+}$ in the sugar-depleted juice of the invention further enhance these effects.

In particular acidification of the sugar-depleted juice and the intestinal milieu by gluconic acid and complex formation with minerals such as calcium, magnesium, potassium, selenium, zinc and iron leads to mineralisation of bone and reduction of blood pressure.

Thus, in a further aspect the invention provides a method for increasing the absorption and retention of dietary minerals or the mineralisation of bone, said method comprising administering a sugar-depleted juice product of the invention to a subject.

Expressed differently, the invention provides a sugar-depleted juice product of the invention for use in increasing the absorption and retention of dietary minerals or the mineralisation of bone in a subject.

Expressed differently, the invention provides for the use of a sugar-depleted juice product of the invention in the manufacture of a medicinal product for use in increasing the absorption and retention of dietary minerals or the mineralisation of bone in a subject.

In turn the invention provides a method for treating perturbations, caused by insufficient absorbance or retention of dietary minerals, in blood coagulation, energy-yielding metabolism, muscle function, neurotransmission, digestive enzyme function, cell division and differentiation, development and maintenance of bones and teeth, blood pressure, the reduction of tiredness and fatigue, electrolyte balance, protein synthesis, psychological function, spermatogenesis, maintenance of hair and nails, immune system function, thyroid function, protection of DNA, proteins and lipids from oxidative damage, DNA synthesis, carbohydrate and macronutrient metabolism, cognitive function, fertility and reproduction, maintenance of serum testosterone concentrations, vitamin A metabolism, formation of red blood cells and haemoglobin, oxygen transport, and cognitive development of children. In particular, increased mineralisation of bone will lead to the effective treatment and prevention of bone loss disorders including osteoporosis and arthritis.

Osmotic effects by non-absorbed gluconate as well as short chain fatty acids released from gluconate utilizing intestinal microorganisms accelerate gastrointestinal transit, soften stools and increase faecal volume. Hence conversion from sugars to gluconate provides foods with effects against constipation. The juice products of the invention may be used to treat constipation and slow GI transit.

"Treatment" when used in relation to the treatment of a medical condition in a subject in accordance with the invention is used broadly herein to include any therapeutic effect, i.e. any beneficial effect on the condition or in relation to the condition. Thus, not only included is eradication or elimination of the condition, or cure of the subject, but also any improvement in the condition. Thus included for example, is an improvement in any symptom or sign of the condition, or in any clinically accepted indicator of the condition (for example, an improvement in the metabolism of glucose). Treatment thus includes both curative and palliative therapy, e.g. of a pre-existing or diagnosed condition, i.e. a reactionary treatment.

"Prevention" as used herein refers to any prophylactic or preventative effect. It thus includes delaying, limiting, reducing or preventing the condition or the onset of the condition, or one or more symptoms or indications thereof, for example relative to the condition or symptom or indication prior to the prophylactic treatment. Prophylaxis thus explicitly includes both absolute prevention of occurrence or development of the condition, or symptom or indication thereof, and any delay in the onset or development of the condition or symptom or indication, or reduction or limitation on the development or progression of the condition or symptom or indication.

Preferably the subject is a human, especially a human suffering from or at risk of developing a disease or conditions recited herein, in other words a human subject in need of the treatments disclosed herein.

The invention will be further described with reference to the following non-limiting Examples in which:

BRIEF DESCRIPTION OF THE DRAWNGS

FIG. 1 shows the measurements of pH and glucose, sucrose, fructose and gluconic acid (g/l) taken during the experiment of Example 1. Invertase is added at 0 hr [101], Glucose oxidase/catalase and 1.25 g/l MgO is added at 12 hrs [102], 1 g/l MgO was added at 12 hrs 30 min [103], 0.2 g/l MgO was added at 13 hrs 50 min [104] and reaction was stopped at 14 hrs 15 min (finished product prior to packaging) [105]. Open squares: fructose; open triangles: free glucose; closed circles: gluconic acid; closed triangles: sucrose; crosses: pH.

Figure 2:
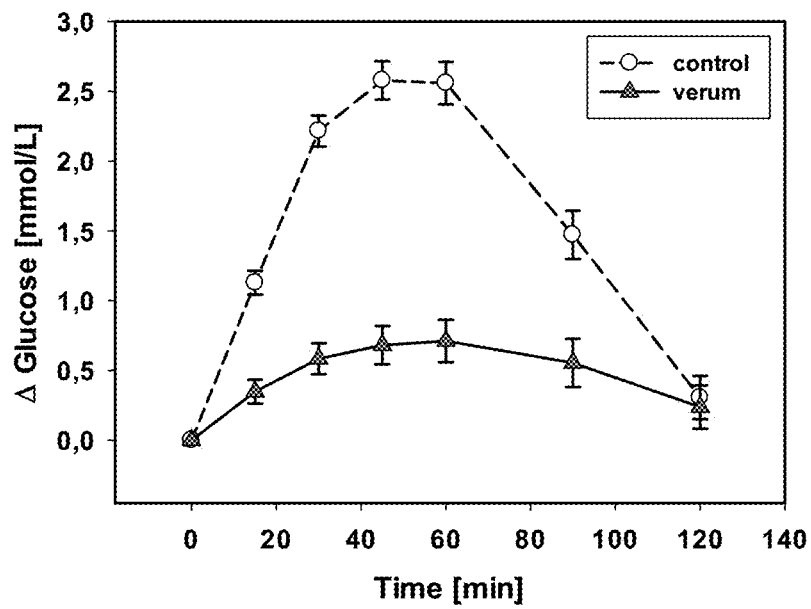
Figure 2:
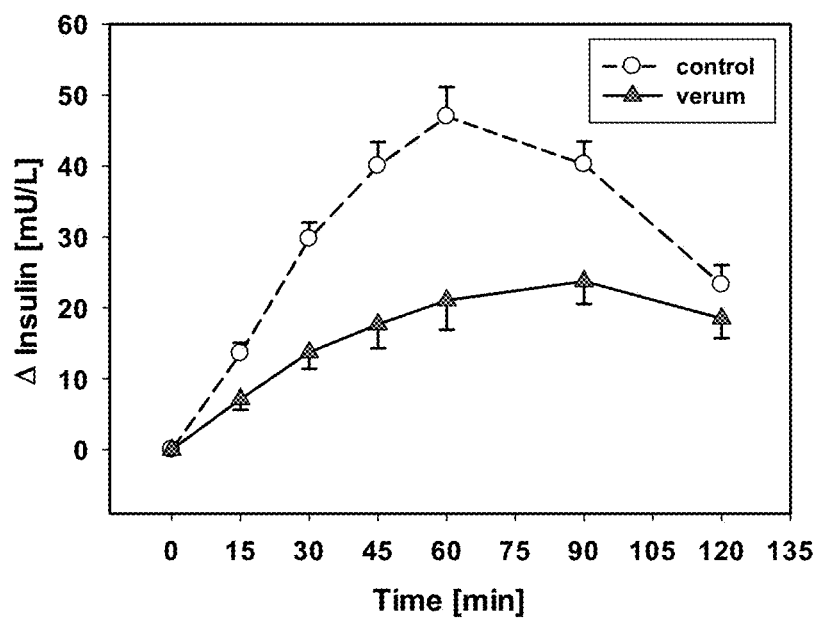

FIG. 2 shows (A) incremental capillary blood glucose and (B) incremental venous plasma insulin levels before and after oral ingestion of 500 mL control apple juice without (control) and a sugar depleted apple juice product of the invention(verum) in 30 men with impaired fasting glucose (IFG). Least square means (LSM)±SEM.

EXAMPLES

Example 1

Preparation of a Sugar Depleted Apple Juice Product

An example of a preferred process and sugar-depleted juice product according to the present invention is exemplified by the following preparation of an apple juice product. Standard large scale apple juice production techniques were first used to produce an apple juice, which was then pasteurised and used in a method according to the present invention to produce a sugar-depleted juice product according to the present invention. Although the preparation of an apple juice product is exemplified herein, this could of course be modified to produce other juice products in accordance with the present invention.

Materials and Methods

A pilot scale production run with three batches has been carried out. Results are shown in FIG. 1 and Table 1. The apples used in the production were 17.5% Red Gravenstein (1400 kg) and the remainder Aroma (6600 kg). All the apples were bought from Sognefrukt B A, Sognefjordvegen 130, 6863 Leikanger. The juice was pressed from the apples and pasteurized. Then invertase (Maxinvert L4000, DSM) was added to 2000 l pasteurized apple juice (0.5 g, 5000 U/l) to split the non-reducing disaccharide sucrose into fructose and glucose over a 12 hour/overnight incubation at ca. 20° C. At the same time a commercially available pectinase was added at 30 g/1000 l, this is the same as standard apple juice production process. To regulate pH prior to glucose oxidase/catalase treatment magnesium hydroxide slurry ($Mg(OH)_2$), made from adding magnesium oxide (MgO) to water, was added until the pH of the juice was about 3.8-4.4. The enzymes glucose oxidase/catalase (as Hyderase L, Amano/Mitsubishi) were added to the juice (0.2 g/l, 3000 U/l) followed by oxygen added and maintained at a concentration in the juice of 3-4 mg/l. pH and oxygen were monitored (data not shown) throughout the glucose oxidase incubation via an automated computer controlled system. pH was maintained at 3.8-4.4 by batch addition of $Mg(OH)_2$ when necessary. A typical incubation time of 3-4 hours at room temperature is sufficient to reduce almost all glucose to gluconic acid. Glucose was monitored over the incubation period by measuring the glucose concentration in juice samples using a rapid and simple reflectometric based kit (Reflectoquant from Merck). The sucrose content after invertase incubation can also be measured in this way. Fructose and gluconic acid were determined via enzymatic assay (r-biopharm). Once most glucose had disappeared all enzyme activity was terminated by pasteurisation. The final product was referred to as a new apple drink, and is a sugar-depleted juice product in accordance with the present invention. A wide range of nutritional and chemical parameters of the finished and packaged products were also determined within 2 months. A reference apple juice (conventional juice) was also analysed simultaneously as a control, and it comprised a blend of equal parts of the same apple juice (1:1:1 by weight) used as the starting juice in each pilot scale production batch.

Results

FIG. 1 discloses the experimental results, and is a typical example of pH, concentration of glucose, sucrose, fructose and gluconic acid monitored during the enzymatic conversion process to make a new apple juice product in accordance with the present invention. The following main findings were shown:

The sucrose content was reduced to levels below the limit of detection by the action of invertase over a period of 12 hours at room temperature. The Limit of Detection is 1 g/L.

The glucose content was slightly increased by the action of invertase on sucrose over a period of 12 hours at room temperature and then significantly reduced to remove almost all glucose by the action of glucose oxidase/over a further 2-3 hour period. Thus the glucose content is decreased significantly from approximately 14 g/L in the conventional control juice to less than 3 g/L in the packaged juice product (mean value of 1.8 g/L over 3 batches tested).

The fructose content was slightly increased by the action of invertase on sucrose over a period of 12 hours at room temperature, and then remained constant during the rest of the production process. Thus, the fructose content in the packaged juice increased by approximately 20% (from approximately 58.2 g/L in the conventional juice) to a mean of 68.7 g/L over 3 batches tested. The extra fructose in the finished and packaged apple juice product may be desirable because it contributes to maintain sweetness.

The sum of sugars in the finished and packaged apple juice product (mean 70.6 g/L over 3 batches) is less than that in the conventional apple juice (96.6 g/L), equating to a reduction of 27%.

The D-gluconic acid content increased to a maximum in the finished product following the action of glucose oxidase/catalase on glucose. In this way nearly all the starting apple juice glucose was converted into gluconic acid in the apple juice product according to the present invention. In the 3 batch experiments, it was shown that the gluconic acid in the packaged juice product is present at a mean of 21.1 g/l compared to below detection limits in the conventional juice. This term "gluconic acid" is generic and represents all the equilibrium species of gluconic acid in an aqueous medium—e.g. lactones, gluconate salts forms, acid.

The magnesium content in the finished packaged juice product was increased to 1200 mg/kg (approximately equivalent to 1.2 g/l) compared to less than the detection limit (<50 mg/kg) in the conventional/reference apple juice.

The Vitamin C content in the finished packaged juice product was decreased from 0.625 mg/100 g in the reference apple juice to an undetectable level (>0.5 mg/100 g).

There was no significant difference between the reference apple juice and the finished packaged apple drink for a range of other chemical parameters e.g. amino acids, vitamins, essential and trace elements, nutrients etc.

It should be noted that the classical industry standard of Brix measurement of free sugar content (sucrose, fructose, glucose) in fruit juice is not appropriate for monitoring the production process according to the present invention because gluconic acid makes an almost identical contribution to the measurement as glucose. Further, the addition of magnesium salt also makes a small contribution to the Brix measurement.

Table 1 below shows analysis of sugar in the 3 production batches of packaged apple juice product according to the present invention, and compares this with conventional apple juice made from the same raw materials. The conventional apple juice meets the requirements for fruit juice laid down by Council Directive 2001/112/EC (Council of the European Union, 2001), and is a representative example of the "starting" material to the juice product according to the present invention.

TABLE 1

Sugar analysis of apple juice product

| Parameter | Units | Sugar-depleted juice product | | | Untreated Juice |
|---|---|---|---|---|---|
| | | Batch 1 | Batch 2 | Batch 3 | |
| Calculation on Sugars | | | | | |
| Sugar free extract (enzymatic) | g/l | 55.0 | 47.1 | 48.3 | 15.1 |
| % sucrose | % | 0 | 0 | 0 | 26 |
| Sum of sugars (enzymatic) | g/l | 71.2 | 73.0 | 67.7 | 96.6 |
| Individual Sugars | | | | | |
| Glucose | g/l | 1.7 | 2.1 | 1.7 | 13.5 |
| Fructose | g/l | 69.4 | 70.8 | 66.0 | 58.2 |
| Sucrose | g/l | <6 | <6 | <6 | 24.9 |
| Sugar Alcohol | | | | | |
| Sorbitol | g/100 g | 0.22 | 0.23 | 0.22 | 0.22 |

Example 2

Glycemic and Insulin Responses to Sugar Depleted Apple Juice Product I

Evidence for a beneficial effect of conversion of glucose to gluconate with the aid of glucose oxidase on postprandial glycemic response to juice is provided by comparing the reference food item of 400 ml apple juice (control) with the test product (400 ml apple juice treated in accordance with the invention) in overweight (BMI 25-30) adult human males. Testing follows the FAO/World Health Organization (WHO) guidelines.

Test products are administered in randomized order. The drinks are ingested within 5 min. Between the tests at least 2 days are interposed. At each visit the capillary blood glucose is measured 9 times over 2 hours by a Haemacue meter. Capillary blood collections and glucose measurements are performed during the two hour interval as the recommended technique to reduce the measurement errors. Blood is drawn twice at baseline and then at times 0 (start of drink), 15 min, 30 min, 45 min, 60 min, 90 min and 120 min.

Venous blood is drawn at baseline, times 0, 15, 30, 45, 60, 90 and 120 min for plasma insulin determination. The incremental AUCs obtained for each test meal are used for comparing the two meals. The 15 incremental AUC obtained for each test meal are used for comparing the two meals. AUC of glycaemic response to treated juice is expressed as percentage of AUC of the response to untreated juice.

Example 3

Glycemic and Insulin Responses to Sugar Depleted Apple Juice Product II

Introduction

This study was designed to assess postprandial glycemic and insulin responses to oral ingestion of a sugar depleted apple juice product of the invention and to directly compare those responses to those of the untreated apple juice. According to the European Food Safety Authority (EFSA) the reduction of post-prandial blood glucose responses may be considered a beneficial physiological effect (e.g. for subjects with impaired glucose tolerance) as long as insulin responses are not disproportionally increased and low post-prandial glycemia is given priority in food choice according to the Food and Agriculture Organization of the United Nations and the World Health Organization.

Subjects and Methods

Design

This mono-center, double-blind, randomized, placebo-controlled, cross-over study was conducted in 30 male volunteers aged ≤18 years presenting with a diagnosed impaired fasting plasma glucose (IFG) of 5.6-6.9mmol/L.

The study received approval from an independent ethics committee (The Ethical Committee of the Medical Council of Schleswig-Holstein, Bad Segeberg, Germany) and was conducted in line with the principles of the current version (2013) of the Declaration of Helsinki (WMA Declaration of Helsinki—Ethical Principles for Medical Research Involving Human Subjects adopted by the 18th WMA (World Medical Association) General Assembly, Helsinki, Finland, June 1964, and amended for the last time by the 64th WMA General Assembly, Fortaleza, Brazil, October 2013, the recommendations for Good Clinical Practice (ICH E6), and in accordance with European and National regulatory requirements.

Subjects

For enrollment the following inclusion criteria had to be fulfilled: Men aged ≤18 years diagnosis of IFG, signed Informed Consent Form. Exclusion criteria were: Current enrollment in another clinical study, enrollment in another clinical study within the last 4 weeks before inclusion, hypersensitivity, allergy or idiosyncratic reaction to apple, apple juice or other apple containing food, acute or chronic infections, renal insufficiency, gastrointestinal illness, history of gastrointestinal surgery, known fructose intolerance, overt diabetes mellitus, endocrine disorders, any disease or condition which might compromise significantly the hematopoietic, renal, endocrine, pulmonary, hepatic, cardiovascular, immunological, central nervous, dermatological or any other body system with the exception of the conditions defined by the inclusion criteria, history of hepatitis B and C, history of HIV infection, history of coagulation disorders or pharmaceutical anti-coagulation (with the exception of acetylsalicylic acid), regular medical treatment including OTC, which may have impact on the study aims (e.g. antidiabetic drugs, laxatives etc.), major cognitive or psychiatric disorders, subjects who are scheduled to undergo hospitalization during the study period, eating disorders (e.g. anorexia, bulimia) or special diets (e.g. vegan, vegetarian), present drug or alcohol abuse, legal incapacity.

The volunteers were free to withdraw from the study at any time without prejudice to their continued care. Specific reasons for discontinuing the study were defined as: Safety reasons as judged by the Investigator, development of specific exclusion criteria during the study, which have impact on subject's safety, incorrect enrollment or randomization of the subject, subject's wish to withdraw prematurely from the study, severe non-compliance to protocol as judged by the Investigator. Individuals withdrawing or discontinuing prematurely before finishing all study visits were supposed to be replaced, in order to have a complete set of 30 subjects having completed all study visits with exploitable results of the primary and secondary parameters.

Random Sequence Generation and Allocation Concealment

Volunteers were randomly assigned to either Verum (sugar-depleted apple juice product of the invention) or Control product (untreated apple juice). In order to avoid selection bias, the randomization scheme was generated by data managers in line with Cochrane guidelines. The randomization list was kept confidential at the premises of Nofima AS and remained confidential with the exception of those involved in product production and statistical managers (after the first part of data locking was performed).

Test Products and Blinding of Participants and Personnel (Table 1)

Control juice. Non-pasteurized conventional apple juice was purchased from Askim Frukt—og Baerpresseri A S, 1815 Askim, Norway. The general apple juice production process includes: dumping, washing and grinding the apples, then pectinase treatment, cold pressing and separation. This control product contained 17 g/L free glucose and ca. 13.5 g/L glucose bound to sucrose (Table 2).

Verum. Sugar depleted apple juice was manufactured as follows. 95 litres of control apple juice was transferred to a kettle with, mixing, heating and cooling options (Proline Touch—Mix Kipgryde, Denmark). With lid the juice was warmed to 85° C. and held at this temperature for 5 min. The juice was then cooled down (running cold water in outer jacket of the kettle) until it was 24° C. Then invertase (Maxinvert L4000, DSM) was added (5000 U/l) to split the non-reducing disaccharide sucrose into fructose and glucose in a overnight incubation at room temperature (ca. 18-21° C.). At the end of the reaction (next morning) the content of sucrose was determined to be <0.1 g/l.

To regulate pH prior to glucose oxidase/catalase treatment calcium hydroxide and potassium hydroxide powder was added. The enzymes glucose oxidase/catalase (as Hyderase L, Amano/Mitsubishi) were added to the juice (3000 U/l) followed by pure oxygen to maintain a constant supply into the reaction tank of 3 mg/l. pH was maintained at 3.6-4.6 by batch addition of calcium hydroxide and potassium hydroxide powders when necessary. An incubation time of 12 hours at room temperature was sufficient to reduce almost all glucose to gluconic acid (remaining glucose <0.1 g/l; Table 2). Glucose was monitored over the incubation period by reflectometric based kit (Reflectoquant from Merck). The sucrose content after invertase incubation was also be measured in this way (0.0 g/l; Table 2). Gluconic acid was determined via enzymatic assay (R-Biopharm). All enzyme activity was terminated by shutting off the oxygen supply. The organoleptic properties were optimized by further addition of calcium and/or potassium hydroxide powder. The final pH of the sugar depleted drink was approximately 4. The final product was pasteurised in a KTM-Troxler (Germany) pasteur and bottled hot, corked, cooled and eventually stored in a fridge.

TABLE 2

Composition of control apple juice and sugar depleted apple juice

| Ingredient | Apple Juice | |
|---|---|---|
| g/L | Untreated (Control) | Sugar depleted (Verum) |
| Glucose | 17 | 0.1 |
| Fructose | 65.2 | 86.3 |
| Sucrose | 26.7 | Below detection limit |
| Sugar* | 109 | 86.4 |
| Gluconic Acid | Below detection limit | 36.4 |
| Calcium | 0.032 | 1.5 |
| Potassium | 0.960 | 3.100 |

Verum and control were similar in flavour, color, texture, and appearance and identical in packaging throughout the study and coded by consecutive numbers in order to avoid performance bias by blinding both study participants and key study personnel including outcome assessors. Code-breaking systems were available in case an adverse event occurred and medical personnel needed to be aware of what the participant received: (verum or control product). Raw data were also blinded during the blind review. The code was broken after the database was locked.

Each study participant consumed 500 mL test product at the morning of the interventional day (Visit 1 and 2). The 500 mL bottle content was shaken well before opening and had to be ingested within 5 minutes.

The test products were provided by Nofima A S, Norway in a brown glass bottles and delivered to Kiel by courier service. The investigating site ensured that the study products were stored safely and properly according to the instructions given by Nofima A S and kept in a secured location to which only the investigator and designated study staff had access. The test products could be stored at room temperature with a shelf-life of two years after production. The shipment and dispensing of study products was recorded in a product accountability log. Monitoring of product accountability was performed by the quality manager after the visits and at the end of the trial.

Procedure/Conduct

Screening visit (V0). Prior to the inclusion procedure (for the assessment of eligibility of the subject), the subject was informed in detail by written information as well as verbally by the investigator about the study and was given the opportunity to ask the Investigator any questions. After signing and dating the Informed Consent Form by both the subject and the investigator subject's identity was verified, the subject's demographics and ethnics were documented, medical history was assessed, concomitant medication and alimentary supplements, smoking and alcohol use were documented, fasting for at least 12 hours was ascertained, vital signs (blood pressure, pulse) and anthropometric data (body weight, body height) were assessed, inclusion and exclusion criteria were assessed and blood samples for confirmation of the inclusion parameter IFG (impaired fasting glucose) were taken. Blood was drawn from the median cubital vein using a 21G butterfly needle. Subjects were requested to appear the next visit after an overnight fasting of at least 12 hours and provided with a subject diary for daily reply regarding adverse event and medication and a questionnaire (EPIC FFQ) for recalling the food frequency with regard to the last 12 month, which had to be completed until the randomization visit.

Impaired fasting glucose (5.6-6.9 mmol/L resp. 100-125 mg/dL) was confirmed by two timely independent measures subjects are eligible for inclusion (one from the data base and one from V0).

Randomization and interventional visit 1 (V1). At V1 the study subjects were randomized and the first intervention was performed. This visit followed V0 within four weeks. Adverse events happening since V0 were documented. If the eligibility of the subject was confirmed by the investigator the subject was randomized. Fasting for 12 hour prior to this visit was checked and an intravenous catheter (Vasofix® Braunüle®, Braun Melsungen, Germany) was inserted into a forearm vein for blood withdrawal at baseline, directly before (time point 0) and 15, 30, 45, 60, 90 and 120 minutes after starting the ingestion of the test product. From all samples plasma insulin was measured. From the blood samples taken at baseline and 120 minutes after consumption of the test product safety parameters were determined (Na, K, Ca, Mg, AST, ALT, γGT, CHE, AP, LDH, CK, bilirubin, creatinine, urea-N, uric acid, complete blood count, cholesterol, HDL-C, LDL-C, triglycerides, CRP). Capillary blood was taken from the finger pad using a HemoCue® Safety Lancet at baseline (twice) and once directly before (time point 0) and 15, 30, 45, 60, 90 and 120 minutes after ingestion of the test product.

Arterial blood pressure, pulse and waist was assessed before and 120 minutes after ingestion. Subjects completed questionnaires on gastrointestinal symptoms (Gastrointestinal Symptom Rating Scale (GSRS)) directly before ingestion (time point 0) with regard to the last three days before the visit day (V1) and with regard to the last hour before starting ingestion. The GSRS was also assessed 60 and 120 minutes after ingestion with respect to the last hours, each. Stool frequency and stool form was assessed directly before ingestion (time point 0) with regard to the last three days before the visit day (V1) and with regard to the last two hours before starting ingestion and also 120 minutes after ingestion with respect to the last two hours. Satiety, hunger, fullness and prospective food consumption were monitored before (time point 0) and 30, 60, 90 and 120 minutes after ingestion using questionnaires.

Subjects were allowed to walk around, sit or lay down, but asked to abstain from eating or drinking or exercising during the test phase. The subjects were surveyed during the whole observation period at the test day and adverse events were monitored.

They were provided with a diary for daily assessment of adverse events and medication. GSRS, stool frequency and stool form were assessed during the three day lasting observation period starting with ingestion of the test drink at visit day V1 and two subsequent days.

Interventional visit 2 (V2): This visit was scheduled on the seventh day after V1 at the earliest. Subjects were requested to return their diaries and questionnaires. Adverse events happening since V1 were documented. Fasting for 12 hour prior to this visit was checked and the test was conducted as described for V1. Again they were provided with a diary for daily assessment of adverse events and medication. GSRS, stool frequency and stool form were assessed during the three day lasting observation period starting with ingestion of the test drink at visit day V1 and two subsequent days. Subjects received a stamped envelope and were requested to send back their diaries and filled questionnaires.

Assessments/Parameters

Primary target parameter: The incremental area under the curve (i$AUC_{120}$) of the capillary blood glucose levels from baseline to 120 min after ingestion of the test drinks (according to FAO/WHO) was defined as primary parameter. Although capillary and venous blood glucose values have been shown to be highly correlated, capillary blood samples is regarded preferable to venous blood samples for reliable GI testing. Glucose was determined using a Hemocue 201 analyzer, Hemocue AB, Ängelholm, Sweden, which had been tested for glycemic index.

Secondary target parameter: The incremental AUC (i$AUC_{120}$) of the plasma insulin levels from baseline to 120 min after ingestion of the test drinks was defined as secondary parameter. Insulin was determined using ELISA (LIASION® Insulin, Diasorin S.p.A, Saluggia, Italy).

Exploratory parameters: The incremental AUC (i$AUC_{60}$) of glucose and insulin levels from baseline to 120 min after ingestion of the test drinks, the postprandial glucose peak $G_{max}$, the amplitude between baseline and $G_{max}$ ($G_{max}-G_{baseline}$) and the maximal amplitude of glucose excursions ($G_{max}-G_{min}$) were calculated for further characterization of postprandial glucose response according to Brand-Miller (Brand-Miller et al, 2009, Am J Clin Nutr, 89: 97-105). Proportional reduction in glycaemic load (Liu, 2000) was calculated by 100-100(i$AUC_{120verum}$×$CH_{verum}$)/(i$AUC_{120control}$×$CH_{control}$), whereby CH was carbohydrate (sugar) content of verum and control, respectively. Postprandial insulin sensitivity was expressed by ISI=2/[AUC insulin×AUC glucose+1] according to Belfiore (Belfiore F, et al., 1998, Mol Genet Metab; 63: 134-141; and Belfiore F., 2000, Diab Care; 23:1595). Satiety, hunger, fullness and prospective food uptake were assessed before and 30, 60, 90 and 120 min after ingestion of test drinks according to established questionnaires.

Plasma sodium, potassium, calcium, magnesium, AST, ALT, γGT, cholinesterase, alkaline phosphatase, LDH, CK, bilirubin, creatinine, urea-N, uric acid, cholesterol, LDL-C, HDL-C, triglycerides, CRP, complete blood count, blood pressure and pulse were measured before and 120 min after ingestion of test drinks.

Three days before and 3 days beginning with ingestion of the test drinks as well as 1 h before and the first and second hour after its ingestion the gastrointestinal symptoms using the GSRS, stool frequency and stool form using Bristol Stool Form Scale were assessed. Bristol Stool Form Scale was transformed by from 1, 2, 3, 4, 5, 6 and 7 to +3, +2, +1, 0, −1, −2 and −3 for expressing deviation from normal.

Adverse events were monitored throughout the total study period and their severity grade (mild, moderate, severe), relationship to the study products (suspected/not suspected), duration (start and end dates or if continuing at final examination), the action taken and its potential categorisation as serious adverse event (SAE) were documented.

Statistical Analysis

Estimation of sample size: Since iAUC data were not available from testing apple juice, sample size estimation was based on data reported by Johnston et al., 2003, Am J Clin Nutr; 78: 728-33. After a 25 g glucose load they found an iAUC=55.6±20.4 (mean±SD) of glycemic response. The glucose content of 500 mL apple juice was expected only about 7(8.5) g, the content of fructose (29.1(33) g, GI=19%) and sucrose (12.5 (13.5) g, GI=68%) summing up to an expected glycemic response $(7+0.19 \times 29.1+0.68 \times 12.5=21.03)(8.5+0.19 \times 33+0.68 \times 13.5=24.0)$ of similar magnitude. We further assumed a reduction in glycemic response by at least 30% by enzymatic treatment of the juice. Assuming a reduction of iAUC by 16.7 and a SD=23.0 of the change and a power of 0.95, a sample size=27 was calculated for paired t-test. Taking the weaknesses of assumptions into account a sample size of n=30 was defined for the trial.

Preventing bias: In order to meet the recommendations of the Cochrane Collaboration for preventing detection bias blinding of outcome assessment was ensured by a blind review of raw data and by un-blinding only after data base was locked, and by conducting statistical analysis in compliance with the statistical analysis plan. In order to avoid attrition bias, distribution of the missing data across intervention groups and the magnitude compared to the effect size were assessed. and missing data were replaced by the Last Observation Carried Forward (LOCF) method using the last post-baseline value for one subject at the previous time. Reporting bias by selective outcome reporting was prevented by the availability of the study protocol and pre-specification of (primary and secondary) outcomes and by adhering to these specifications.

Definition of sets to be analysed: The Intention-To-Treat (ITT) collective was defined to comprise all subjects randomized and having taken at least one dose of the test products (intervention 1 at V1). The Per-protocol (PP) Set comprised all subjects randomized, who have no major protocol deviation.

Tests: The baseline and demographic characteristics of the two groups with different order of intervention (verum-control versus control-verum) were compared using Student t or Mann-Whitney test as appropriate depending on distribution of data. Verum and control were compared by repeated measures ANOVA, in order to take cross-over design and potential effects by the order of intervention into account. The significance level of the primary and secondary parameters was adjusted to multiple testing according to Bonferroni-Holm.

Results

Subject Characteristics

Distribution of volunteers through the study: N=51 subjects having had IFG in previous studies at the study site were screened for meeting inclusion criteria and for exclusion criteria. In N=19 IFG was not verified and in N=1 individual an allergy was reported which was not reported before. Thus N=20 subjects were excluded at screening and N=31 were enrolled. Between screening visit (V0) and randomization (V1) an erysipela occurred in N=1 individual. There were no drop-outs and no major deviations from study protocol. Thus the per protocol population (PP) was identical with intent-to-treat population (ITT) and N=30 individuals, who were supposed to complete all study visits according to the study protocol with exploitable results of the primary and secondary parameters (PP), actually completed the study.

Population characteristics at baseline (Table 3): The total population (ITT and PP) showed features of the metabolic syndrome. The baseline characteristics in the group with the order verum-control (VC) did not differ from those in the group with the order control-verum (CV).

TABLE 3

Population characteristics at baseline

| (Mean ± SEM) | Total Group (n = 30) | Group Order VC (n = 15) | Group Order CV (n = 15) | t-Test/ Mann-Whitney Test* |
|---|---|---|---|---|
| Age [years] | 68.0 ± 2.4 | 68.7 ± 1.4 | 67.4 ± 1.9 | p = 0.602 |
| Body Height [m] | 178.0 ± 1.8 | 177.9 ± 2.0 | 178.1 ± 1.5 | p = 0.911 |
| Body Weight [kg] | 100.2 ± 4.2 | 98.3 ± 3.3 | 102.0 ± 5.1 | p = 0.542 |
| BMI [kg/m$^2$] | 31.6 ± 1.2 | 31.1 ± 1.0 | 32.1 ± 1.5 | p = 0.581 |
| Waist [cm] | 110.9 ± 2.3 | 110.3 ± 2.7 | 111.8 ± 3.7 | p = 0..699 |
| Syst. Blood Pressure [mmHg] | 131.7 ± 3.9 | 129.3 ± 3.9 | 134.0 ± 3.8 | p = 0.403 |
| Diastol. Blood Pressure [mmHg] | 81.8 ± 1.8 | 81.0 ± 2.0 | 82.7 ± 1.6 | p = 0.524 |
| Fasting Plasma Glucose [mmol/L] | 6.04 ± 0.1 | 6.0 ± 0.1 | 6.08 ± 0.1 | *p = 0.467 |
| Fasting Plasma Triglycerides [mg/dL] | 166.8 ± 17.9 | 163.6 ± 22.0 | 169.9 ± 28.9 | p = 0.864 |
| Fasting Plasma HDL-C [mg/dL] | 49.3 ± 1.8 | 49.5 ± 2.4 | 49.2 ± 2.7 | p = 0.927 |

Characteristics of groups whereby those of the group with the order verum-control (VC) were compared with those of the group with the order control-verum (CV) by Student t test in case of normal distribution of data and by *Mann-Whitney test, if data were not normally distributed.

Composition of Test Products (Table 2)

By enzymatic treatment glucose and sucrose were mostly removed from apple juice by enzymatic treatment, whereas fructose increased after cleavage of sucrose by invertase. The sugar content in g/L was reduced by 21%. The pH-value was similar between verum and control after addition of potassium and calcium hydroxides to the enzymatically treated juice. Potassium and calcium content accordingly differed between verum and control.

Postprandial Glycemia (FIG. 2, Table 4)

The curves of capillary blood glucose levels after ingestion of the test drinks differed considerably between verum and control (FIG. 2B). The iAUC$_{120}$ of glucose (primary parameter) differed significantly between verum and control. Similar differences were seen for iAUC$_{60}$, glucose maxima, the postprandial increase from baseline and the maximal glucose excursion (Table 4). The order of intervention had no impact indicating that there were no significant carry-over effects (Table 4). By enzymatic treatment of apple juice glycemic response to its oral ingestion was significantly reduced by 68% resulting in a reduction of glycemic load by 74.9%.

TABLE 4

Glycemic and insulin response to apple juice without (control) and with enzymatic treatment (verum)

| Parameter | Verum (N = 30) | Control (N = 30) | V versus C p | Carry-Over Effect p |
|---|---|---|---|---|
| iAUC$_{120}$ Glucose [min × mmol/L] | 63.6 ± 12.3 | 198.0 ± 12.3 | <0.001 | 0.806 |
| iAUC$_{60}$ Glucose [min × mmol/L] | 29.7 ± 5.3 | 108.0 ± 5.3 | <0.001 | 0.945 |
| Gmax [mmol/L] | 6.97 ± 0.21 | 8.77 ± 0.21 | <0.001 | 0.876 |
| Gmax − Gbase [mmol/L] | 0.984 ± 0.141 | 2.796 ± 0.141 | <0.001 | 0.701 |
| Gmax − Gmin [mmol/L] | 1.157 ± 0.141 | 3.026 ± 0.141 | <0.001 | 0.579 |
| iAUC$_{120}$ Insulin [min × mU/L] | 2045 ± 285 | 3864 ± 285 | <0.001 | 0.608 |
| iAUC$_{60}$ Insulin [min × mU/L] | 739 ± 125 | 1603 ± 125 | <0.001 | 0.401* |
| ISI ×10$^6$ | 32.2 ± 3.83 | 4.36 ± 3.83 | <0.001 | 0.471 | iAUC$_{120}$ Glucose and iAUC$_{60}$ Glucose express the incremental area under the curve of capillary blood glucose levels from ingestion to 120 and 60 min, respectively, after that.
Gmax is the postprandial peak glucose level.
Gmax − Gbase express the increase of glucose level from baseline to Gmax.
Gmax − Gmin express the maximal glucose excursion.
iAUC$_{120}$ Insulin and iAUC$_{60}$ Insulin express the incremental area under the curve of venous plasma insulin levels from ingestion to 120 and 60 min, respectively, after that.
ISI = 2/[AUC insulin × AUC glucose + 1] after Belfiore.
P was assessed by ANOVA RM;
*Normality failed Postprandial Insulin (FIG. 2, Table 4)

The curves of venous plasma insulin levels after ingestion of the test drinks differed considerably between verum and control (FIG. 2B). The iAUC$_{120}$ (secondary parameter) differed significantly. By enzymatic treatment of apple juice insulin response to its oral ingestion was reduced by 47%. Similar differences between verum and control were seen for iAUC$_{60}$ (Table 4). Postprandial insulin sensitivity as assessed by ISI differed, too (Table 4). The order of intervention had no impact indicating that there were no significant carry-over effects (Table 4).

Postprandial Safety Parameters

Plasma sodium, potassium, calcium, magnesium, AST, ALT, γGT, cholinesterase, alkaline phosphatase, LDH, CK, bilirubin, creatinine, urea-N, uric acid, cholesterol, LDL-C, HDL-C, CRP, complete blood count, blood pressure and pulse did not show clinically relevant changes and remained within the normal range 120 min after ingestion of test drinks.

Postprandial Satiety, Hunger, Fullness and Prospective Food Uptake

Satiety, hunger and prospective food uptake did not differ, neither in the fasting state nor postprandially. Fullness differed in the fasting state between verum (12.9±4.7) and control (24.7±4.7)(p=0.04; ANOVA RM), but no longer in the following, postprandial assessments.

Gastrointestinal Symptoms

GSRS: Gastrointestinal symptoms, as assessed by the Gastrointestinal Symptom Rating Scale (GSRS), did not differ 1 hour before ingestion of the drinks, neither the total score, nor any of the dimensions pain, reflux, indigestion, diarrhoea or constipation. Within the first hour after ingestion the total score was higher (p=0.028) in case of verum (1.140±0.038) compared to control (1.053±0.038) and the indigestion score was also higher (1.275±0.083) versus 1.117±0.083; p=0.008). During the second hour after ingestion no differences between verum and control were seen. This held true within the 3 days period beginning with ingestion of the test drinks.

Stool frequency did not differ between verum and control within the two hours before ingestion, but was higher (p=0.009) 2 hours after verum (0.567±0.123) compared to control (0.467±0.123). Accordingly stool form, as assessed by a transformed Bristol Stool Form Scale, was looser (p=0.002) after verum (−1.20±0.23) than after control (−0.67±0.23). Within the 3 days period beginning with ingestion of the test drinks no differences were reported, neither in stool frequency nor in stool form. In none of the volunteers diarrhoea as defined by WHO (three or more loose stools per day) occurred.

Discussion

By enzymatic treatment of apple juice its sugar content in g/L could be reduced by 21% and glycemic and insulin response to oral ingestion was significantly reduced by 68% and 47%, respectively resulting in a reduction of glycemic load by 74.9%.

The invention claimed is:

1. A method for preparation of a sugar-depleted fruit or vegetable juice product wherein said sugar-depleted juice product is a juice, puree, paste or stew, wherein said fruit or vegetable is not a grain, wherein said sugar-depleted juice product contains at least about 5 g/l gluconic acid, and said sugar-depleted juice product contains any two or three, of a mass concentration of (i) at least 0.5 g/l Ca$^{2+}$,
(ii) at least 1 g/l K$^+$, and
(iii) at least 0.1 g/l Mg$^{2+}$.

said method comprising providing a fruit or vegetable juice product containing free glucose and/or sucrose and:

(a) contacting said juice product with an enzyme which hydrolyses sucrose to glucose and fructose,
(b) contacting the enzyme treated juice product of step (a) with an enzyme which converts glucose into gluconic acid, and
(c) supplementing said juice product with a source of Ca$^{2+}$, a source of Mg$^{2+}$ and/or a source of K$^+$ in an amount sufficient to give said mass concentrations of Ca$^{2+}$, Mg$^{2+}$ and/or K$^+$, respectively, wherein steps (a) and/or (b) may be performed simultaneously with step (c) or before or after step (c); or said method comprising providing a sucrose-depleted fruit or vegetable juice product containing free glucose and:

(d) contacting said juice product with an enzyme which converts glucose into gluconic acid, and
(e) supplementing said juice product with a source of Ca$^{2+}$, a source of Mg$^{2+}$ and/or a source of K$^+$ in an amount sufficient to give said mass concentrations of Ca$^{2+}$, Mg$^{2+}$ and/or K$^+$, respectively, wherein steps (d) and (e) may be performed simultaneously or separately in any order; or said method comprising providing a sucrose-depleted fruit or vegetable juice product containing free glucose and said mass concentrations of any two or three of Ca$^{2+}$, Mg$^{2+}$ and/or K$^+$, respectively, and:

(f) contacting said juice with an enzyme which converts glucose into gluconic acid; or said method comprising providing a free glucose-depleted fruit or vegetable juice product, wherein said juice product contains sucrose and at least about 5 g/l gluconic acid and:
(g) contacting said juice product with an enzyme which hydrolyses sucrose to glucose and fructose, and
(h) supplementing said juice product with a source of $Ca^{2+}$, a source of $Mg^{2+}$ and/or a source of $K^+$ in an amount sufficient to give said mass concentrations of $Ca^{2+}$, $Mg^{2+}$ and/or $K^+$, respectively,
wherein steps (g) and (h) may be performed simultaneously or separately in any order; or
said method comprising providing a free glucose-depleted fruit or vegetable juice product, wherein said juice product contains sucrose, at least about 5 g/l gluconic acid and said mass concentrations of any two or three of $Ca^{2+}$, $Mg^{2+}$ and/or $K^+$, respectively and:
(i) contacting said juice product with an enzyme which hydrolyses sucrose to glucose and fructose; or
said method comprising providing a free glucose and optionally sucrose depleted fruit or vegetable juice product, wherein said juice product contains at least about 5 g/l gluconic acid and:
(j) supplementing said juice product with a source of $Ca^{2+}$, a source of $Mg^{2+}$ and/or a source of $K^+$ in an amount sufficient to give said mass concentrations of $Ca^{2+}$, $Mg^{2+}$ and/or $K^+$, respectively; or
said method comprising providing a fruit or vegetable juice product containing free glucose and/or sucrose and said mass concentrations of any two or three of $Ca^{2+}$, $Mg^{2+}$ and/or $K^+$, respectively, and:
(k) contacting said juice product with an enzyme which hydrolyses sucrose to glucose and fructose, and
(l) contacting the enzyme treated juice of step (k) with an enzyme which converts glucose into gluconic acid,
wherein steps (k) and (l) may be performed simultaneously or separately; or
said method comprising providing a fruit or vegetable juice product containing free glucose and optionally sucrose, and:
(m) contacting said juice product with an enzyme which converts glucose into gluconic acid, and
(n) supplementing said juice product with a source of $Ca^{2+}$, a source of $Mg^{2+}$ and/or a source of $K^+$ in an amount sufficient to give said mass concentrations of any two or three of $Ca^{2+}$, $Mg^{2+}$ and/or $K^+$, respectively,
wherein steps (m) and (n) may be performed simultaneously or separately in any order; or
said method comprising providing a fruit or vegetable juice product containing free glucose and optionally sucrose and said mass concentrations of any two or three of $Ca^{2+}$, $Mg^{2+}$ and/or $K^+$, respectively, and:
(o) contacting said juice product with an enzyme which converts glucose into gluconic acid.

2. The method of claim 1, wherein said source of $Ca^{2+}$, $Mg^{2+}$ and/or $K^+$ are selected from halide salts, organic salts; oxides, hydroxides, sulphates, phosphates, nitrites, nitrates, and carbonates.

3. The method of claim 1, wherein oxygen is supplied during one of more steps.

4. The method of claim 3, wherein the oxygen is supplied in the form of pure $O_2$.

5. The method of claim 1, wherein said enzyme which converts glucose into gluconic acid is a glucose oxidase.

6. The method of claim 4, wherein the step of contacting the juice product with the glucose oxidase takes place in the presence of a hydrogen peroxide degrading enzyme.

7. The method of claim 6, wherein the hydrogen peroxide degrading enzyme, is a catalase.

8. The method of claim 5, wherein the step of contacting the juice product with the glucose oxidase takes place at about pH 3-6.

9. The method of claim 8, wherein said pH is controlled by one or more of the sources of $Ca^{2+}$, $Mg^{2+}$ and/or $K^+$, wherein the sources are selected from halide salts, organic salts; oxides, hydroxides, sulphates, phosphates, nitrites, nitrates, and carbonates.

10. The method of claim 1, wherein the combined mass concentration of free glucose and sucrose in the sugar-depleted juice product is no more than 20 g/l when said sugar-depleted juice product is adjusted in volume with water to give a gluconic acid concentration of 5 g/l to 100 g/l.

11. The method of claim 1, wherein the sugar-depleted juice product contains no more than 5 g/l free glucose, and no more than 5 g/l sucrose, when said juice product is adjusted in volume with water to give a gluconic acid concentration of 5 g/l to 100 g/l.

12. The method of claim 1, wherein the sugar-depleted juice product is essentially devoid of free glucose and sucrose.

13. The method of claim 1, wherein the sugar-depleted juice product contains 5 to 100 g/l gluconic acid.

14. The method of claim 13,
wherein the sugar-depleted juice product contains 0.5 to 10 g/l $Ca^{2+}$,
wherein the sugar-depleted juice product contains 1 to 20 g/l $K^{30}$,
wherein the sugar-depleted juice product contains 0.1 to 2 g/l $Mg^{2+}$,
or a combination thereof.

15. A method for the preparation of a free-glucose and sucrose-depleted fruit or vegetable juice product, wherein said juice product is a fruit or vegetable juice or a juice-retaining fruit or vegetable derived matter, and wherein said fruit or vegetable is not a grain, wherein said free-glucose and sucrose-depleted juice product contains at least about 5 g/l gluconic acid and said free-glucose and sucrose-depleted juice product contains any two or three, of a mass concentration of
(i) at least 0.5 g/l $Ca^{2+}$,
(ii) at least 1 g/l $K^+$, and
(iii) at least 0.1 g/l $Mg^{2+}$,
said method comprising providing a fruit or vegetable juice product containing free glucose and/or sucrose and:
(a) contacting said juice product with an enzyme which hydrolyses sucrose to glucose and fructose,
(b) contacting the enzyme treated juice product of step (a) with an enzyme which converts glucose into gluconic acid, and
(c) supplementing said juice product with a source of $Ca^{2+}$, a source of $Mg^{2+}$ and/or a source of $K^+$ in an amount sufficient to give said mass concentrations of $Ca^{2+}$, $Mg^{2+}$ and/or $K^+$, respectively,
wherein steps (a) and/or (b) may be performed simultaneously with step (c) or before or after step (c); or
said method comprising providing a sucrose-depleted fruit or vegetable juice product containing free glucose and:

(d) contacting said juice product with an enzyme which converts glucose into gluconic acid, and (e) supplementing said juice product with a source of $Ca^{2+}$, a source of $Mg^{2+}$ and/or a source of $K^+$ in an amount sufficient to give said mass concentrations of $Ca^{2+}$, $Mg^{2+}$ and/or $K^+$, respectively, wherein steps (d) and (e) may be performed simultaneously or separately in any order; or said method comprising providing a sucrose-depleted fruit or vegetable juice product containing free glucose and said mass concentrations of any two or three of $Ca^{2+}$, $Mg^{2+}$ and/or $K^+$, respectively, and:

(f) contacting said juice with an enzyme which converts glucose into gluconic acid; or said method comprising providing a free glucose-depleted fruit or vegetable juice product, wherein said juice product contains sucrose and at least about 5 g/l gluconic acid and:

(g) contacting said juice product with an enzyme which hydrolyses sucrose to glucose and fructose, and (h) supplementing said juice product with a source of $Ca^{2+}$, a source of $Mg^{2+}$ and/or a source of $K^+$ in an amount sufficient to give said mass concentrations of $Ca^{2+}$, $Mg^{2+}$ and/or $K^+$, respectively, wherein steps (g) and (h) may be performed simultaneously or separately in any order; or said method comprising providing a free glucose-depleted fruit or vegetable juice product, wherein said juice product contains sucrose, at least about 5 g/l gluconic acid and said mass concentrations of any two or three of $Ca^{2+}$, $Mg^{2+}$ and/or $K^+$, respectively and:

(i) contacting said juice product with an enzyme which hydrolyses sucrose to glucose and fructose; or said method comprising providing a free glucose and sucrose depleted fruit or vegetable juice product, wherein said juice product contains at least about 5 g/l gluconic acid and:

(j) supplementing said juice product with a source of $Ca^{2+}$, a source of $Mg^{2+}$ and/or a source of $K^+$ in an amount sufficient to give said mass concentrations of $Ca^{2+}$, $Mg^{2+}$ and/or $K^+$, respectively; or said method comprising providing a fruit or vegetable juice product containing free glucose and sucrose and said mass concentrations of any two or three of $Ca^{2+}$, $Mg^{2+}$ and/or $K^+$, respectively, and:

(k) contacting said juice product with an enzyme which hydrolyses sucrose to glucose and fructose, and (l) contacting the enzyme treated juice of step (k) with an enzyme which converts glucose into gluconic acid, wherein steps (k) and (l) may be performed simultaneously or separately.

16. The method of claim 15, wherein said source of $Ca^{2+}$, $Mg^{2+}$ and/or $K^+$ are selected from halide salts, organic salts; oxides, hydroxides, sulphates, phosphates, nitrites, nitrates, and carbonates.

17. The method of claim 15, wherein oxygen is supplied during one of more steps.

18. The method of claim 17, wherein the oxygen is supplied in the form of pure $O_2$.

19. The method of claim 15, wherein said enzyme which converts glucose into gluconic acid is a glucose oxidase.

20. The method of claim 19, wherein the step of contacting the juice product with the glucose oxidase takes place in the presence of a hydrogen peroxide degrading enzyme.

21. The method of claim 20, wherein the hydrogen peroxide degrading enzyme, is a catalase.

22. The method of claim 19, wherein the step of contacting the juice product with the glucose oxidase takes place at about pH 3-6.

23. The method of claim 22, wherein said pH is controlled by one or more of the sources of $Ca^{2+}$, $Mg^{2+}$ and/or $K^+$, wherein the sources are selected from halide salts, organic salts; oxides, hydroxides, sulphates, phosphates, nitrites, nitrates, and carbonates.

24. The method of claim 15, wherein the combined mass concentration of free glucose and sucrose in the free-glucose and sucrose-depleted juice product is no more than 20 g/l when said juice product is adjusted in volume with water to give a gluconic acid concentration of 5 g/l to 100 g/l.

25. The method of claim 15, wherein the free-glucose and sucrose-depleted juice product contains no more than 5 g/l free glucose, and no more than 5 g/l sucrose, when said juice product is adjusted in volume with water to give a gluconic acid concentration of 5 g/l to 100 g/l.

26. The method of claim 15, wherein the free-glucose and sucrose-depleted juice product is essentially devoid of free glucose and sucrose.

27. The method of claim 15, wherein the free-glucose and sucrose-depleted juice product contains 5 to 100 g/l gluconic acid.

28. The method of claim 27,
wherein the free-glucose and sucrose-depleted juice product contains 0.5 to 10 g/l $Ca^{2+}$,
wherein the free-glucose and sucrose-depleted juice product contains 1 to 20 g/l $K^+$,
wherein the free-glucose and sucrose-depleted juice product contains 0.1 to 2 g/l $Mg^{2+}$,
or a combination thereof.

* * * * *